US009960441B2

(12) United States Patent
Antonelli

(10) Patent No.: US 9,960,441 B2
(45) Date of Patent: *May 1, 2018

(54) SYNTHESIS AND HYDROGEN STORAGE PROPERTIES OF NOVEL MANGANESE HYDRIDES

(71) Applicant: University of South Wales Commercial Services, Ltd., Wales (GB)

(72) Inventor: David Antonelli, Cardiff (GB)

(73) Assignee: UNIVERSITY OF SOUTH WALES COMMERCIAL SERVICES LTD., Wales (GB)

( * ) Notice: Subject to any disclaimer, the term of this patent is extended or adjusted under 35 U.S.C. 154(b) by 200 days.

This patent is subject to a terminal disclaimer.

(21) Appl. No.: 14/304,317

(22) Filed: Jun. 13, 2014

(65) Prior Publication Data

US 2014/0370406 A1 Dec. 18, 2014

Related U.S. Application Data

(60) Provisional application No. 61/835,071, filed on Jun. 14, 2013.

(51) Int. Cl.
| | |
|---|---|
| H01M 8/065 | (2016.01) |
| H01M 4/24 | (2006.01) |
| C01B 3/00 | (2006.01) |
| C01B 6/02 | (2006.01) |
| C07F 13/00 | (2006.01) |

(52) U.S. Cl.
CPC ............. *H01M 8/065* (2013.01); *C01B 3/001* (2013.01); *C01B 3/0015* (2013.01); *C01B 6/02* (2013.01); *C07F 13/00* (2013.01); *H01M 4/242* (2013.01); *C01B 2203/0272* (2013.01); *C01B 2203/066* (2013.01); *C01B 2203/1211* (2013.01); *Y02E 60/327* (2013.01); *Y02E 60/328* (2013.01)

(58) Field of Classification Search
CPC ........ C01B 3/0078; C01B 6/02; H01M 8/065; H01M 4/242
See application file for complete search history.

(56) References Cited

U.S. PATENT DOCUMENTS

| | | | | |
|---|---|---|---|---|
| 4,894,301 | A * | 1/1990 | Dyer ................... | H01L 27/0214 429/101 |
| 5,906,792 | A | 5/1999 | Schulz et al. | |
| 7,625,547 | B2 | 12/2009 | Wolverton | |
| 9,376,316 | B2 * | 6/2016 | Antonelli ............. | C01B 3/0078 |
| 9,391,334 | B2 * | 7/2016 | Barton ................ | H01M 8/0606 |
| 2001/0051130 | A1 | 12/2001 | Jensen et al. | |
| 2004/0105805 | A1 | 6/2004 | Zidan | |
| 2004/0229090 | A1 | 11/2004 | Davis et al. | |
| 2005/0180916 | A1 | 8/2005 | Autrey et al. | |

| | | | |
|---|---|---|---|
| 2006/0003203 | A1 | 1/2006 | Wang et al. |
| 2007/0025908 | A1 | 2/2007 | Sandrock et al. |
| 2008/0138675 | A1 | 6/2008 | Jang et al. |
| 2009/0227808 | A1 | 9/2009 | Kim et al. |
| 2010/0022791 | A1 | 1/2010 | Ihm et al. |
| 2010/0036145 | A1 | 2/2010 | Kim et al. |
| 2010/0184595 | A1 * | 7/2010 | Vajo ...................... C01B 3/0042 502/406 |
| 2010/0247424 | A1 | 9/2010 | Mao et al. |
| 2011/0201834 | A1 | 8/2011 | Kim et al. |
| 2013/0181162 | A1 | 7/2013 | Antonelli |
| 2014/0370406 | A1 | 12/2014 | Antonelli |

FOREIGN PATENT DOCUMENTS

| | | |
|---|---|---|
| CN | 2861702 Y | 1/2007 |
| CN | 201233436 Y | 5/2009 |
| EP | 0283359 A1 | 9/1988 |
| EP | 0374015 A2 | 6/1990 |
| EP | 2098530 A1 | 9/2009 |
| EP | 2154105 A1 | 2/2010 |
| GB | 1577830 A | 10/1980 |
| JP | 2006298670 A | 11/2006 |
| JP | 201043082 | 2/2010 |
| JP | 2010503662 A | 2/2010 |
| KR | 20100031446 A | 3/2010 |
| WO | WO-2007015597 A1 | 2/2007 |
| WO | WO-2008032985 A1 | 3/2008 |
| WO | WO-2008094007 A1 | 8/2008 |
| WO | WO-2010072002 A1 | 7/2010 |
| WO | WO-2010085108 A2 | 7/2010 |
| WO | WO 2011/026201 * | 3/2011 |
| WO | WO-2013088170 A1 | 6/2013 |

OTHER PUBLICATIONS

Balabanov, N., Boggs, J.—Ab Initio Study of Structure and Spectra of MnH2, MnH2-, and MnH3, J. Phys Chem A 2002, 106, pp. 6839-6843.*
Hood, D.M., Pitzer, R.M., Schaefer, H.F—Electronic structure of homoleptic transition metal hydrides:TiH4, VH4, CrH4, MnH4, FeH4, CoH4, and NiH4, J. Chem. Phys. 71(2), Jul. 15, 1979.*
Jagtoyen, M., Pardue, J., Rantell, T., Grulke, E., Derbyshire, F.—Porosity of Carbon Nanotubes, date unknown.*
Choudhury, P.—Theoretical and Experimental Study of Solid State Complex Borohydride Hydrogen Storage Materials, 2009.*
Schulzke, et al., The Unusual Stability of Homoleptic Di- and Tetravalent Chromium Alkyls, *Organometallics*, 3810-3816, 2002.
Matuso, et al., First-principles Studies of Complex Hydride YMn2H6 and Its Synthesis from Metal Hydride YMn$_2$H$_{4.5}$, Applied Physics Letters, American Institute of Physics, 98:22:221908, 2011.
Gamo, et al., Formation and Properties of Titanium-manganese Alloy Hydrides, International Journal of Hydrogen Energy, Elseview Science Publishers B.V., 10:1:39-47, 1985.

(Continued)

*Primary Examiner* — Anca Eoff
(74) *Attorney, Agent, or Firm* — Blank Rome LLP

(57) ABSTRACT

This disclosure relates to novel manganese hydrides, processes for their preparation, and their use in hydrogen storage applications. The disclosure also relates to processes for preparing manganese dialkyl compounds having high purity, and their use in the preparation of manganese hydrides having enhance hydrogen storage capacity.

47 Claims, 13 Drawing Sheets

(56) References Cited

OTHER PUBLICATIONS

Ozin, et al., Synthesis of Ligand-free Transition-metal Dihydrides in Low-temperature Matrixes: Manganese Dihydride $MnH_2$, Journal of the American Chemical Society, 106:3:807-809, 1984.

International Search Report issued in PCT/GB2014/051825 dated Oct. 8, 2014.

Alberola, et al., Bis[(Trimethylsilyl]Manganese: Structural Variations of Its Solvent-Free and TMEDA-, Pyridine-, and Dioxane-Complexed Forms, Organometallics, 2009, 28, 2112-2118.

Andersen, et al., Bis(Neopentyl)-, Bis(trimethylsilylmethyl)- and Bis(2-methyl-2-phenyl-propyl)-magnesium, J.C.S. Dalton, 1977, 809-811.

Andersen, et al., Neopentyl, Neophyl, and Trimethylsilylmethyl Compounds of Manganese, Manganese (II) Dialkyls; Manganese (II) Dialkyl Amine Adducts; Tetra-alkylmanganate(II) Ions and Lithium Salts, Manganese IV) Tetra-alkyls, J.C.S. Dalton, 1976, 2204-2211.

Andersen, et al., The Molecular Structure of Monomeric Base-Free Bis(neopentyl)manganese by Gas Electron Diffraction, J. Chem. Soc., Chem. Commun., 1985, 1807-1808.

Andrews, Matrix Infrared Spectra and Density Functional Calculations of Transition Metal Hydrides and Dihydrogen Complexes, Chem. Soc. Rev., 2004, 33, 123-132.

Badding, et al., High-Pressure Chemistry of Hydrogren in Metals: In Situ Study of Iron Hydride, Science, 1991, 253, 421-424.

Balabanov, et al., Ab Initio Study of Structure and Spectra of MnH2, MnH2-, and MnH3, J. Phys. Chem. A, 2002, 106, 6839-6843.

Barker, et al., Silylmethyl and Related Complexes, Part 6. Preparation, Properties, and Crystal and Molecular Structure of Tris[bis(trimethylsilyl)methyl]-chromium(III); the Chemistry of Related Compounds of Titanium(III) Vanadium(III), Zirconium(IV), and Hafnium(IV), J.C.S. Dalton, 1978, 734-740.

Buijink, et al., Electron-Deficient Vanadium Alkyl Complexes: Synthesis and Molecular Structure of the Vanadium(III) Dinitrogen Complex [(Me3CCH2)3V]2(?-N2), Organometallics, 1993, 2004-2005.

Cahiez et al., Chemistry of Organomanganese(II) Compounds, Chem. Rev., 2009, 109:3, 1435-1476.

Cahiez, et al., Organomangaense(II) Reagents XVII: Preparation of Organomanganese Bromide Compounds in Either: An Efficient and Economic Alternative to Organomanganese Iodide Compounds for Synthetic Applications, Tetrahedron Letters, 1989, 30:27, 3545-3546.

Cahiez, et al., Reactivity of Organomanganese(II) Reagents: II. A New, Convenient Preparation of Alkyl, Alkenyl, and Alkynyl Ketones via Organomangaese(II) Iodides, Synthesis Communications, 1977, 130-133.

Cahiez, et al., Salt Effects on the Reactivity and the Stability of Organomanganese Reagents, Tetrahedron Letters, 1998, 39, 849-852.

Cantrell, Phase Composition and the Effect of Thermal Cycling for VHx, V0.995C0.005Hx, and V0.975Zr0.020C0.005Hx, J. Alloys and Compounds, Feb. 1-14, 1999, available online at http://hdl.handle.net/2014/17065.

Chertihin, et al., Infrared Spectra of FeH, FeH2, and FeH3 in Solid Argon, J. Phys. Chem., 1995, 99, 12131-12134.

Chertihin, et al., Reactions of Laser Ablated Ti Atoms with Hydrogen During Condensation in Excess Argon, Infrared Spectra of the TiH, TiH2, TiH3, and TiH4 Molecules, J. Am. Chem. Soc., 1994, 116, 8322-8327.

Coates, et al., Some t-Butylmagnesium and Related Complexes, Reactions Between Hydrides and Organomagnesium Compounds, J. Chem. Soc. (A), 1968, 514-518.

Dilts, et al., The Nature of Soluble Copper(I) Hydride, Journal of the American Chemical Society, 1968, 90:21, 5769-5772.

Dolgoplosk, et al., Preparation of -Alkenyl and -Organometallic Compounds of Transition Metals and Study of their Properties, Organic Chemistry, 1978, Plenum Publishing Corporation, 2315-2328.

Eckert, et al., IV.D.1 Hydrogen Storage Material with Binding Intermediate Between Physisorption and Chemisorption, FY 2007 Annual Progress Report, DOE Hydrogen-Program, 587-592.

El-Kurdi, Homoleptic Alkyl- and Aryl-Complexes of Transition Metals (Ti, Zr, Hf, Nb, and Cr) and Tetra-organyloxyvanadium-(V) and -(IV) Complexes, Inaugural-Dissertation, Dept. Biology, Chemistry and Pharmacy, Freie Universitat Berlin, Sep. 2010.

Fedotov, et al., Atomic Ordering in the hcp Cobalt Hydrides and Deuterides, Journal of Alloys and Compounds, 1999, 291, 1-7.

Fischer, et al., Reinvestigation of Arylmanganese Chemistry—Synthesis and Molecular Structures of [(thf)4Mg(–Cl)2Mn(Br)Mes], [Mes(thf)Mn(–Mes)]2, and (MnPh2)∞ (Ph = C6H5; Mes = Mesityl, 2,4,6-Me3C6H2), Journal of Organometallic Chemistry, 2009, 694, 1107-1111.

Friour, et al., Organomanganous Reagents: IX, Preparation of Various Halogenated, Alkoxylated, Aryloxylated, and Arylsulfenylated Ketones from Correspondingly Functionalized Carboxylic Acid Chlorides or Anyhdrides, Synthesis Communications, 1984, 37-40.

Gambarotta, et al., A Homoleptic Arylmanganese (II) Complex: Synthesis and Structure of a Thermally Stable Trinuclear Mesitylmanganese (II) Complex, J. Chem. Soc., Chem. Commun., 1983, 1128-1129.

Hamaed et al., Hydride-Induced Amplification of Performance and Binding Enthalpies in Chromium Hydrazide Gels for Kubas-Type Hydrogen Storage, J. Am. Chem. Soc., 133, 15434-15443, 2011.

Hoang et al., Design and Synthesis of Vanadium Hydrazide Gels for Kubas-Type Hydrogen Adsorption: A New Class of Hydrogen Storage Materials, J. Am. Chem. Soc., 132(33), 11792-11798, 2010.

King, Structure and Bonding in Homelpetic Transition Metal Hydride Anions, Coordination Chemistry Reviews 2000, 200-202, 813-829.

Klose, et al., Insertion Reactions of Isocyanides and Nitriles into Unsupported Iron-Aryl Bonds: The Synthesis of a Dimeric Iron(II) Homeleptic Iminoacyl Complex, Organometallics, 1993, 12, 2414-2416.

Korsgen, et al., The Identification of the FeH2 Radical in the Gas Phase by Infrared Spectroscopy, J. Chem. Phys. 1996, 104:12, 4859-4861.

Korsgen, et al., The Infrared Spectrum of FeH2, Studied in the Gas Phase by Laser Magnetic Resonance, Journal of Chemical Physics, 1999, 110:8, 3861-3869.

Love, et al., A Non-Metallocene Hydride of Titanium(III), J. Chem. Soc., 1999, 121, 6843-6849.

Meunier, et al., Synthesis and Characerization of Titanium Hydride Thin Films Obtained by Reactice Cathodic Sputtering, Materials Science and Engineering, 1993, B18, 303-307.

Miller, et al., Laser Photoelectron Spectroscopy of MnH2–, FeH2–, CoH2–, and NiH2–: Determination of the Electron Affinities for the Metal Dihydrides, J. Chem. Phys., 1996, 84:8, 4127-4131.

Mowat, et al., Elimination Stabilized Alkyls, Part I. Chromium, Molybdenum, Tungsten and Vanadium, J.C.S. Dalton, 1972, 533-542.

Noh, et al., Rhenium Oxohalides: Synthesis and Crystal Structures of ReO3Cl(Thf)2, ReOCl4(THF), Re2O3Cl6(THF)2, and Re2O3Cl6(H2O)2, The Royal Society of Chemistry, Dalt. Trans., 2007, 674-679.

Ozin, et al., The Photoreverisble Oxidative-Addition, Reductive-Elimination Reactions Fe + H2 ⟵⟶ FeH2 in Low-Temperature Martrices, J. Phys. Chem. 1984, 88, 645-648.

Peddada, et al., Hydride Precipitation in Vapor Deposited Ti Thin Films, J. Mater. Res., 1993, 8:2, 291-296.

Rathman, et al., Amazing Base-Mesityllithium, MESLi, Fine, Specialty & Performance Chemicals, 2003, 6-8.

Rubinovitz, et al., The Photochemical Fe + H2 Reaction in Ar and Kr Matrices by Irradiation in the Visible Region, J. Phys. Chem., 1986, 90, 1940-1944.

Sakintuna et al., Metal Hydride Materials for Solid Hydrogen Storage: A Review. International Journal of Hydrogen Energy, 32, 1121-1140, 2007.

Skipper et al., The Kubas Interaction in M(II) (M = Ti, V, Cr) Hydrazine-Based Hydrogen Storage Materials: A DFT Study, Dalton Trans., 41(28), 8515-8523, 2012.

(56) References Cited

OTHER PUBLICATIONS

Stepien, Formation of Cobalt Hydrides in Low Temperature Field Evaporation, Optica Applicata, 2005, XXXV:3, 363-368.

Takashi, Reaction of Titanium Trichloride with Amines, Notes, 1967, 40, 4, 9-1000.

Van Zee, et al., High Spin Molecules: ESR and Optical Spectroscopy of MnH (7 ) and MnH2 (6A1) at 4° K, J. Chem. Phys. 1978, 69:5, 1869-1875.

Van Zee, et al., MnF2 and MnH2 Molecules (S=5/2): "Extra" Lines in Their ESR Spectra, Chemical Physics Letters, 1979, 64:2, 325-327.

Wang, et al., Matrix Infrared Spectra and Density Functional Theory Calculations of Manganese and Rhenium Hydrides, J. Phys. Chem. A, 2003, 107, 4081-4091.

Zucchini, et al., Synthesis and Properties of Some Titanium and Zirconium Benzyl Derivatives, Journal of Organometallic Chemistry, 1971, 26, 357-372.

E. E.Krasovskii et al., Electronic Structure of Early Transition Metal Dihydrides and Hypothetical ScH3, TiH3 and VH3 Compounds, Int. J. Hydrogen Energy, 1995, vol. 20, No. 5, pp. 373-376.

Buyoung MA et al., Periodic Trends for Transition Metal Dihydrides MH2, Dihydride Dihydrogen Complexes MH2/H2, and Tetrahydrides MH4 (M=Ti, V, and Cr), J. Am. Chem. Soc., 1996, vol. 118, No. 4, pp. 870-879.

Antonov, et al., Neutron Spectroscopy of γ Manganese Hydride, Solid State Communications, 2000, 113:569-572.

Hoang, et al., Observation of TiH5 and TiH7 in Bulk-Phase TiH3 Gels for Kubas-Type Hydrogen Storage, Chem. Matter., 2013, 25:4765-4771.

Kyoi, et al., Novel Magnesium-Manganese Hydrides Prepared by the Gigapascal High Pressure Technique, Materials Transaction, 2002, 43:5:1124-1126.

Marinin, et al., Hydrogen Sorption Properties of Hexagonal Laves Phase TiMn1,5 Intermetallic Compound, 228-229.

Morris, et al., On the Path to Bulk FeH2: Synthesis and Magnetic Properties of Amorphous Iron (II) Hydride, Journal of Alloys and Compounds, 2014, 590:199-204.

Morris, et al., Thermodynamically Neutral Kubas-type Hydrogen Storage Using Amorphous Cr(III) Alkyl Hydride Gels, Phys. Chem. Chem. Phys., 2015, 17:9480-9487.

Pearse, et al., Band Spectrum of Manganese Hydride, MnH, Nature Publishing Group, 1937, 590.

\* cited by examiner

SYNTHESIS AND HYDROGEN STORAGE PROPERTIES OF NOVEL MANGANESE HYDRIDES

This application claims the benefit of U.S. Provisional Application No. 61/835,071, filed Jun. 14, 2013, the entire contents of which are hereby incorporated by reference.

FIELD OF THE INVENTION

The present invention relates to novel manganese hydrides, processes for their preparation, and their use in hydrogen storage applications. The present invention also relates to processes for preparing manganese dialkyl or diaryl compounds having high purity, and their use in the preparation of manganese hydrides that exhibit enhanced hydrogen storage capacity when used as hydrogen storage systems.

BACKGROUND OF THE INVENTION

The enormous demands placed on the world's fossil fuel reserves have led to concerns regarding global warming, energy security and environmental pollution. Researchers continue to seek alternative fuel sources. Molecular hydrogen is ideal in this regard because it is lightweight, abundant, has more than three times the energy density by mass than currently used hydrocarbon fuels such as gasoline, and its only combustion product (water) is environmentally benign. Despite the advances made in fuel cell technology and hydrogen production, storage remains a great hurdle. See, e.g., R. H. Wiswall et al., *Science*, 186, 1158, 1974; S. Orimo et al., *Chem. Rev.*, 107, 4111, 2007, and L. K. Heung, On-board Hydrogen Storage System Using Metal Hydride, *HYPOTHESIS II*, 1, 1997. Using current technology, hydrogen storage has a low energy storage density by volume relative to hydrocarbon fuels. Therefore, with all other factors being equal, in order to store the same amount of energy, hydrogen storage requires a much larger and heavier storage tank than hydrocarbon fuel storage.

Gravimetric capacity is a measure of the amount of hydrogen that can be stored per unit mass of the storage system. Volumetric capacity is a measure of the amount hydrogen that can be stored per unit volume of the storage system. The United States Department of Energy (DOE) has set targets for hydrogen storage. The 2017 target set by the DOE for hydrogen storage is 5.5 wt. % and 40 kg/m$^3$ volumetric adsorption for a fully reversible system operating near room temperature. The ultimate goals are 7.5 wt % and 70 kg/m$^3$.

To date no technology has satisfied all the requirements set out by the DOE. Some technologies being considered involve the use of chemical carriers such as alloys, adsorbents such as amorphous carbons (see, e.g., R. Yang et al., *J. Am. Chem. Soc.*, 131, 4224, 2009), zeolites (see, e.g., A. Pacula, et al., *J. Phys. Chem. C*, 112, 2764, 2008) and metal organic frameworks (MOFs) (see, e.g., K. M. Thomas, *Dalton Trans.*, 1487, 2009; S. S. Kaye et al., *J. Am. Chem. Soc.*, 129, 14176, 2007, and N. L. Rosi et al., Science, 300, 1127, 2003).

The use of metal hydrides, such LiH and NaAlH$_4$ is thwarted by heat management issues and problems with slow kinetics and/or reversibility. For example, when hydrogen reacts with magnesium or a sodium-aluminum alloy to give a metal hydride such as MgH$_2$ and NaAlH$_4$, significant amounts of heat are given off. When this heat is produced, a cooling step must be carried out to prevent a significant rise in temperature in the system, and this cooling step constitutes an energy loss to the system. Furthermore, heating is typically necessary to remove the hydrogen when required. This is an artifact of the high enthalpies of hydrogen binding (>60 kJ/mol) typical of hydrides such as MgH$_2$ and NaAlH$_4$.

Compression techniques have been used to increase gas pressure and improve the energy storage density by volume for hydrogen. This allows for the storage tanks to be smaller. However, compressing hydrogen requires a significant amount of energy, often accounting for as much as 30% of the stored energy. Furthermore, large pressure vessels are required for such compression techniques.

Another technique for storing hydrogen involves converting hydrogen gas to liquid hydrogen. This technique requires cryogenic storage because hydrogen has a very low boiling point (−252.88° C.). The liquefaction of hydrogen requires a large amount of energy to maintain these extremely low temperatures. Furthermore, the storage tank for liquid hydrogen requires complex and expensive insulation in order to prevent the liquid hydrogen from evaporating. In addition, liquid hydrogen has a lower energy density by volume than hydrocarbon fuels, such as gasoline, by a factor of about 4.

Physisorption materials, such as amorphous carbons and metal organic frameworks (MOFs), achieve promising storage capacities at temperatures of 77 K, but typically lose approximately 90% of their performance at room temperature due to low heats of adsorption (typically 5-13 kJ/mol H$_2$). See, e.g., A. Dailly et al., *J. Phys. Chem. B*, 110, 1099, 2006, J. Rowsell et al., *Angew. Chem., Int. Ed.*, 2005, 4670, 2005. In order to achieve the DOE target under ambient conditions, the ideal H$_2$ binding energy is predicted to be in the range of 20-30 kJ/mol per hydrogen molecule. See, e.g., R. Lochan et al., *Phys. Chem. Chem. Phys.*, 8, 1357, 2006. Moreover, energy production costs for the preparation of hydrogen storage materials may be an important factor.

There is, therefore, a need for improved, lower cost materials that can be used as hydrogen storage systems. Additionally, there is a need for improved methods to synthesize materials of higher purity that exhibit enhanced hydrogen storage capacity when used as hydrogen storage systems.

SUMMARY OF THE INVENTION

The inventor has surprisingly developed a manganese hydride material having high hydrogen storage capacity. It was discovered that relatively large amounts of organic and/or metal residues are not required to maintain the structure of the material and permit hydrogen to enter and exit the material during absorption and desorption cycles. To the contrary, the inventor has discovered that the removal of these residues permits increasingly high hydrogen capacity. Without wishing to be bound by any particular theory, the inventor theorizes that the materials include amorphous polymeric chains which permit hydrogen (H$_2$) to flow in and out of the material while also permitting the manganese centres to form interactions (e.g., Kubas interactions) with one or more H$_2$ molecules to produce, for example, MnH$_x$, wherein x is, e.g., about 2.8 to about 10, such as about 3.8 to about 10.

The inventor has also found that transition metal dialkyl or diaryl complexes (e.g., manganese dialkyl or diaryl complexes, such as bis(neopentyl)manganese) may be prepared in high yield and high purity via reaction of a metal halide dioxane complex (e.g., a dichloro manganese dioxane complex, such as MnCl$_2$(dioxane)$_{1.3-1.5}$) with an alkyl Grignard (e.g., (neopentyl)magnesium chloride), a dialkyl magnesium compound (e.g., bis(neopentyl)magnesium), or a combination thereof, in an ether solvent (e.g., diethyl ether, diisopropyl ether and dibutyl ether). Notably, the reaction may be performed in one step (starting from the metal halide such as MnCl$_2$). The processes described herein are suitable for commercial scale up and do not require multiple purification steps in order to obtain a high purity product.

Hydrogenation of the resulting metal dialkyl or diaryl complexes (such as bis(neopentyl)manganese) affords metal hydride frameworks that interact with hydrogen to form solid state hydrides (such as the hydrides MnH$_x$, wherein x is about 2.8 to about 10 (such as from about 3.8 to about 10), e.g., x is about 2.8 to about 3.2, about 3.8 to about 4.2, about 4.8 to about 5.2, about 5.8 to about 6.2, about 6.8 to about 7.2, about 7.8 to about 8.2, about 8.2 to about 9.2 or about 9.8 to about 10.2, e.g., MnH$_3$, MnH$_4$, MnH$_5$, MnH$_6$, MnH$_7$, MnH$_8$, MnH$_9$ or MnH$_{10}$ (for further example, x is about 3.8 to about 4.2, about 5.8 to about 6.2, about 7.8 to about 8.2, or about 9.8 to about 10.2, such as, e.g., MnH$_4$, MnH$_6$, MnH$_8$, MnH$_{10}$) and can reversibly release hydrogen, thereby acting as materials for hydrogen storage. The metal hydrides described herein are stable as bulk solids at room temperature (i.e., exhibit low pyrophoricity and reduced air sensitivity), which are important features for practical hydrogen storage. Furthermore, all components used in the synthesis of the metal hydrides described herein may be recycled.

The Metal Hydrides

The metal hydrides of the present invention are capable of absorbing molecular hydrogen (H$_2$) in an amount of at least about 2%, at least about 3%, at least about 4%, at least about 5%, at least about 6%, at least about 7%, at least about 8%, at least about 9%, at least about 10%, at least about 11%, at least about 12%, at least about 13% or at least about 14%, e.g., in an amount up to about 14%, such as from about 2.0% to about 14.0%, from about 8.0% to about 12.0%, or about 3.5%, about 7.0%, about 10.5%, about 14%) based upon 100% total weight of the metal hydride without molecular hydrogen stored in it.

In one embodiment, the present invention relates to a metal hydride of the formula (I):

$$Mn(M^2)_zH_xR_yL_n \quad (I)$$

wherein

M$^2$ is one or more metals (other than manganese), which have a total content of z (e.g., one or more metals (e.g. doping metals), such as, for example, lithium, sodium, magnesium, calcium, beryllium, iron, titanium, vanadium, chromium, manganese, cobalt, copper, zinc, gallium, nickel, zirconium, niobium, molybdenum, technetium, ruthenium, rhodium, palladium, silver, cadmium, hafnium, tantalum, tungsten, rhenium, osmium, iridium, platinum, gold, mercury, and combinations thereof);

R, if present, is an organic group (e.g., an organic alkyl group without a β-hydrogen substituent, such as, for example, mesityl, neopentyl, trimethylsilylmethyl or benzyl);

L is a Lewis base (e.g., an organic solvent (such as an ether solvent, e.g. Et$_2$O, dioxane, THF), water, H$_2$S, an amine, a phosphine, a sulfide, and combinations thereof);

n is 0 to about 1 (e.g., about 0 to about 0.8, 0 to about 0.6, 0 to about 0.5, 0 to about 0.4, 0 to about 0.2, about 0 to about 0.1, about 0 to about 0.05 or about 0 to about 0.01);

x is about 1.5 to about 10 (e.g., about 2 to about 10, about 4 to about 10, about 6 to about 10 or about 8 to about 10, such as about 2, about 3, about 4, about 5, about 6, about 7, about 8, about 9 or about 10, for further example, about 2, about 4, about 6, about 8 or about 10);

y is 0 to about 0.25 (e.g., about 0 to about 0.2, about 0 to about 0.1, about 0 to about 0.05 or about 0 to about 0.01); and z is 0 to about 1, (e.g., 0 to about 0.75, 0 to about 0.5, 0 to about 0.25, 0 to about 0.2, 0 to about 0.1 or 0 to about 0.05).

In one embodiment, the organic group R does not contain a β-hydrogen substituent (e.g., R is mesityl, neopentyl, trimethylsilylmethyl or benzyl). In a preferred embodiment, R is neopentyl or mesityl.

In one embodiment, z is 0.

In one embodiment, n is 0.

In one embodiment, x is about 1.8 to about 2.2, e.g., about 2; about 3.8 to about 4.2, e.g., about 4; about 5.8 to about 6.2, e.g., about 6; about 7.8 to about 8.2, e.g., about 8, or about 9.8 to about 10.2, e.g., about 10. For example, in one embodiment x is about 1.8 to about 2.2, e.g., about 2.

In another embodiment, x is about 2.8 to about 3.2, e.g., about 3; about 4.8 to about 5.2, e.g., about 5; about 6.8 to about 7.2, e.g., about 7 or about 8.8 to about 9.2, e.g., about 9.

In another embodiment, x is selected from the group consisting of (i) about 1.8 to about 2.2, (ii) about 2.2 to about 2.8, (iii) about 2.8 to about 3.2, (iv) about 3.2 to about 3.8, (v) about 3.8 to about 4.2, (vi) about 4.2 to about 4.8, (vii) about 4.8 to about 5.2, (viii) about 5.2 to about 6.8, (ix) about 6.8 to about 7.2, (x) about 7.2 to about 7.8, (xi) about 7.8 to about 8.2, (xii) about 8.2 to about 8.8, (xiii) about 8.8 to about 9.2, (xiv) about 9.2 to about 9.8, and (xv) about 9.8 to about 10.2.

In another embodiment, x is selected from the group consisting of (i) about 1.8 to about 2.2, (ii) about 2.8 to about 3.2, (iii) about 3.8 to about 4.2, (iv) about 4.8 to about 5.2, (v) about 6.8 to about 7.2, (vi) about 7.8 to about 8.2, (vii) about 8.8 to about 9.2 and (viii) about 9.8 to about 10.2.

In another embodiment, x is about 1.8 to about 2.2. In another embodiment, x is about 2.8 to about 3.2. In another embodiment, x is about 3.8 to about 4.2. In another embodiment, x is about 4.8 to about 5.2. In another embodiment, x is about 5.8 to about 6.2. In another embodiment, x is about 6.8 to about 7.2. In another embodiment, x is about 7.8 to about 8.2. In another embodiment, x is about 8.8 to about 9.2. In another embodiment, x is about 9.8 to about 10.2.

In one embodiment, when x is greater than about 2 (e.g., when x is greater than about 3.8), the material is at a pressure of about 10 bar or more of hydrogen (e.g., at about 15 bar, at about 20 bar, at about 25 bar, at about 30 bar, at about 40 bar, at about 50 bar, at about 75 bar, at about 85, about 100, about 125 or about 150 bar of hydrogen, or higher).

In another embodiment, the present invention relates to a metal hydride of formula (II):

$$Mn(M^2)_zH_xR_yL_n \quad (II)$$

wherein

M$^2$ is one or more metals (other than manganese), which have a total content of z (e.g., one or more metals (e.g. doping metals), such as lithium, sodium, magnesium, calcium, beryllium, iron, titanium, vanadium, chromium, manganese, cobalt, copper, zinc, gallium, nickel, zirconium, niobium, molybdenum, technetium, ruthenium, rhodium, palladium, silver, cadmium, hafnium, tantalum, tungsten, rhenium, osmium, iridium, platinum, gold, mercury, and combinations thereof);

R, if present, is an organic group (e.g., an organic alkyl group without a β-hydrogen substituent, such as mesityl, neopentyl, trimethylsilylmethyl or benzyl);

L is a Lewis base (e.g., an organic solvent (such as an ether solvent, e.g. $Et_2O$, dioxane, THF), water, $H_2S$, an amine, a phosphine, a sulfide, and combinations thereof);

n is 0 to about 1 (e.g., about 0 to about 0.8, 0 to about 0.6, 0 to about 0.5, 0 to about 0.4, 0 to about 0.2, about 0 to about 0.1, about 0 to about 0.05 or about 0 to about 0.01);

x is about 0.1 to about 2.2, (such as about 1.8 to about 2.2, e.g., about 1.9 to about 2.1, about 1.95 to about 2.05, or about 2);

y is 0 to about 0.25 (e.g., about 0 to about 0.2, about 0 to about 0.1, about 0 to about 0.05 or about 0 to about 0.01); and z is 0 to about 0.2 (e.g., 0 to about 0.1 or 0 to about 0.05); wherein (1) the metal hydride is capable of absorbing hydrogen ($H_2$) in an amount of at least 2.0% (e.g., in an amount up to about 14%, such as from about 2.0% to about 14.0%, from about 4.0% to about 14.0%, from about 6.0% to about 14.0%, from about 8.0% to about 14.0%, from about 10.0% to about 14.0%, or about 3.5%, about 7.0%, about 10.5%, about 14%) (based upon 100% total weight of the metal hydride without hydrogen stored in it).

In one embodiment, the organic group R does not contain a β-hydrogen substituent (e.g., R is mesityl, neopentyl, trimethylsilylmethyl or benzyl). In a preferred embodiment, R is neopentyl or mesityl.

In one embodiment, z is 0.

In one embodiment, n is 0.

In one embodiment, x is about 2.

In one embodiment of any metal hydrides described herein, y is less than about 0.2, such as less than about 0.1, less than about 0.05, less than about 0.01 or less than about 0.005. In one embodiment, y is 0.

In additional embodiments of any of the hydrides described herein R, when present, is not a polymeric group.

In one embodiment, the metal hydride is $MnH_x(neopentyl)_yL_n$ wherein L, n, x and y are as defined in any of the embodiments above regarding Formulas (I) and (II).

In another embodiment, the present invention relates to manganese dihydride that is free or substantially free of metal ions (other than manganese). In another embodiment, the present invention relates to manganese dihydride that is free or substantially free of organic residue (e.g., organic ligands or solvents used during the synthesis of the manganese dihydride or a precursor thereof). In another embodiment, the present invention relates to manganese dihydride that is free or substantially free of metal ions (other than manganese) and free or substantially free of organic residue (e.g., organic ligands or solvents used during the synthesis of the manganese dihydride or a precursor thereof).

In another embodiment, any of the metal hydrides described herein has a Brunauer-Emmett-Teller (BET) surface area (measured by nitrogen adsorption) of less than about 5 $m^2/g$, such as less than about 4 $m^2/g$, such as less than about 3 $m^2/g$, less than about 2 $m^2/g$ or less than about 1.5 $m^2/g$, such as about 1.4 $m^2/g$.

In one embodiment, the metal hydride of the present invention is $Ma_{1.8-2.2}R_yL_n$, $MnH_{3.8-4.2}R_yL_n$, $MnH_{5.8-6.2}R_yL_n$, $Mn_{7.8-8.2}R_yL_n$ or $MnH_{9.8-10.2}R_yL_n$ wherein R, L and n are as defined in any embodiment above, and y, in each case, is independently from 0 to about 0.2 (e.g., from about 0 to about 0.1, about 0 to about 0.05, about 0 to about 0.01 or about 0 to about 0.005). In one embodiment, y is, in each case, independently, 0.

In another embodiment, the metal hydride of the present invention is $MnH_{2.8-3.2}R_yL_n$, $MnH_{4.8-5.2}R_yL_n$, $MnH_{6.8-7.2}R_yL_n$ or $MnH_{8.8-9.2}R_yL_n$ wherein R, L and n are as defined in any embodiment above, and y, in each case, is independently from 0 to about 0.2 (e.g., from about 0 to about 0.1, about 0 to about 0.05, about 0 to about 0.01 or about 0 to about 0.005). In one embodiment, y is, in each case, independently, 0.

In another embodiment, any of the metal hydrides described herein may contain a transition metal in more than one oxidation state (e.g., Mn(II)/Mn(IV)).

In one embodiment, any of the metal hydrides described herein are capable of absorbing molecular hydrogen ($H_2$) in an amount of at least about 2%, at least about 3%, at least about 4%, at least about 5%, at least about 6%, at least about 7%, at least about 8%, at least about 9%, at least about 10%, at least about 11%, at least about 12%, at least about 13% or at least about 14%, e.g., in an amount up to about 14%, such as from about 2.0% to about 14.0%, from about 8.0% to about 12.0%, or about 3.5%, about 7.0%, about 10.5%, about 14%) based upon 100% total weight of the metal hydride without molecular hydrogen stored in it.

In another embodiment, the metal hydride is capable of absorbing molecular hydrogen ($H_2$) in an amount of from about 2.0, 2.5 or 3.0% to about 4.0, 4.5 or 5.0%, e.g., about 3.5% (based upon 100% total weight of the metal hydride without hydrogen stored in it).

In another embodiment, the metal hydride is capable of absorbing molecular hydrogen ($H_2$) in an amount of from about 5.0, 5.5 or 6.0% to about 8.0, 8.5 or 9.0%, e.g., about 7.5% (based upon 100% total weight of the metal hydride without hydrogen stored in it).

In another embodiment, the metal hydride is capable of absorbing molecular hydrogen ($H_2$) in an amount of from about 8.5, 9.0 or 9.5% to about 10.5, 11.0 or 11.5%, e.g., about 10.5% (based upon 100% total weight of the metal hydride without hydrogen stored in it).

In another embodiment, the metal hydride is capable of absorbing molecular hydrogen ($H_2$) in an amount of from about 12.5 13.0 or 13.5% to about 14% (based upon 100% total weight of the metal hydride without hydrogen stored in it).

In one embodiment, the metal hydrides of formula (I) or (II) described herein comprise greater than about 25 wt. % of $MnH_x$ (wherein x is as described in any embodiment herein), such as greater than about 30 wt. %, greater than about 40 wt. %, greater than about 50 wt. %, greater than about 60 wt. %, greater than about 70 wt. %, greater than about 75 wt. %, greater than about 80 wt. %, greater than about 85 wt. %, greater than about 90 wt. %, greater than about 95 wt. %, greater than about 99 wt. %, greater than about 99.5 wt. % of $MnH_x$.

In one embodiment of the metal hydrides of formula (I) or (II) described herein, the ratio of Mn—H (manganese-hydrogen) bonds to Mn—C (manganese-carbon) bonds in the metal hydrides is greater that about 2:1, such as greater that about 2.5:1, greater that about 5:1, greater that about 10:1, greater that about 20:1, greater that about 25:1, greater that about 50:1, greater that about 75:1, greater that about 100:1, greater that about 250:1.

In one embodiment of any of the metal hydrides described herein, the metal hydride is capable of coordinating with $H_2$. For example, in one embodiment of any of the metal hydrides described herein, the metal hydride is capable of coordinating with $H_2$ via a Kubas interaction.

The metal hydrides described herein preferably have sufficient microporosity to permit $H_2$ to move in and out of the metal hydride framework to the active binding sites. In one embodiment, the present invention relates to a metal hydride storage material comprising a metal hydride of any of the embodiments described herein, where the material has sufficient microporosity to permit: (i) $H_2$ to diffuse in and out of the material and the active binding sites of the metal hydride; (ii) the metal to coordinate with $H_2$ via, for example, a Kubas interaction; and (iii) absorption of $H_2$ in an amount of about 2.0% to about 14.0% (based upon 100% total weight of the metal hydride without hydrogen stored in it). The metal hydride storage material may be incorporated into a hydrogen storage system as described herein.

In yet another embodiment, any of the metal hydrides described herein is crystalline.

In one embodiment, the metal hydrides described herein are amorphous or substantially amorphous (e.g., contain less than about 20% crystallinity, such as less than about 10%, less than about 5%, less than about 2.5%, less than about 1% or less than about 0.5% crystallinity) as measured by X-ray diffraction using a Cu Kα radiation (40 kV, 40 mA) source. Metal hydrides having closed packed structures are desirable due to their higher volumetric densities, so long as they permit diffusion of $H_2$ to the metal binding sites within them. Where the closed packed structure of a metal hydride does not permit diffusion of $H_2$ to the metal binding sites, the metal hydride preferably does not have a closed packed structure. The metal hydride may be in the form of a gel or solid.

In one embodiment, any of the metal hydrides described herein is a solid (e.g., a bulk solid), for example, a stable bulk solid at room temperature.

In another embodiment, any of the metal hydrides described herein may contain a minor amount (e.g., up to 0.5 moles total) of an impurity selected from phosphines (e.g., trimethylphosphine), ethers, water, alcohols, amines, sulfides, nitrides, and combinations thereof. The phosphine (e.g., trimethylphosphine), ether, alcohol, amine or sulfide residues may remain from their use in the synthesis of the metal hydride or may be formed as byproducts during the synthesis. In one embodiment, any of the metal hydrides of the present invention may contain less than about 10.0 wt %, less than about 9.0 wt %, less than about 9.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.4 wt %, less than about 0.3 wt %, less than about 0.25 wt %, less than about 0.2 wt %, less than about 0.1 wt %, less than about 0.05 wt %, less than about 0.01 wt %, less than about 0.005 wt % or less than about 0.001 wt % of a phosphine (e.g., trimethylphosphine), ethers (e.g., $Et_2O$, THF, dioxane), water, alcohol, amine, sulfide or nitride residue, or a combination thereof. In a preferred embodiment, the metal hydride is free or substantially free of a phosphine (e.g., trimethylphosphine), ethers, water, alcohol, amine, sulfide or nitride residue, or a combination thereof. In addition, in embodiments of the invention where impurities are found, the metal hydrides described herein may also contain minor amounts (e.g., up to 0.5 moles total) of metal hydroxides (M-OH) and metal ethers (M-O-M) from the hydrolysis of metal alkyl species with residual water contained within the reaction mixture.

In certain embodiments, any of the metal hydrides of the present invention contain less than about 10.0 wt % of lithium or magnesium, or a combination thereof. These lithium and magnesium residues may remain from their use in the synthesis of the metal hydride. For example, any of the metal hydrides of the present invention may contain less than about 9.0 wt %, less than about 8.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.25 wt %, less than about 0.1 wt % or less than about 0.05 wt %, less than about 0.01 wt %, less than about 0.005 wt %, or less than about 0.001 wt % of lithium or magnesium or a combination thereof. In another embodiment, any of the metal hydrides of the present invention contain less than about 0.5 wt % of lithium or magnesium, or a combination thereof. For example, any of the metal hydrides of the present invention may contain less than about 0.4 wt %, less than about 0.3 wt %, less than about 0.25 wt %, less than about 0.2 wt %, less than about 0.1 wt %, less than about 0.05 wt %, less than about 0.01 wt %, less than about 0.005 wt % or less than about 0.001 wt % of lithium or magnesium or a combination thereof. In a preferred embodiment, the metal hydride is free or substantially free of lithium or magnesium, or a combination thereof.

The metal hydrides of the present invention may contain halogen. For instance, the metal hydride may contain less than about 10.0 wt % of a halogen (such as Br⁻, Cl⁻, or I⁻). These halogen residues may remain from their use in the synthesis of the metal hydride (for instance, from the use of a Grignard reagent). For example, any of the metal hydrides of the present invention may contain less than about 9.0 wt %, less than about 8.0 wt %, less than about 7.5 wt %, less than about 5.0 wt %, less than about 4.0 wt %, less than about 3.0 wt %, less than about 2.0 wt %, less than about 1.0 wt %, less than about 0.75 wt %, less than about 0.5 wt %, less than about 0.25 wt %, less than about 0.1 wt % less than about 0.05 wt %, less than about 0.01 wt %, less than about 0.005 wt %, or less than about 0.001 wt % of halogen. In a preferred embodiment, the metal hydride is free or substantially free of halogen.

Synthesis

In one embodiment, the present invention relates to a process for preparing a manganese alkyl compound of the formula (III)

$$MnR_xY_yL_n \qquad (III)$$

wherein

R is an organic group (e.g., an organic alkyl group without a β-hydrogen substituent, such as mesityl, neopentyl, trimethylsilylmethyl, or benzyl);

L is a Lewis base (e.g., an organic solvent (such as an ether solvent, e.g. $Et_2O$, dioxane, THF), water, $H_2S$, an amine, a phosphine, a sulfide, and combinations thereof);

n is 0 to about 1 (e.g., 0 to about 0.8, 0 to about 0.6, 0 to about 0.5, 0 to about 0.4, 0 to about 0.2, 0 to about 0.1, 0 to about 0.05 or 0 to about 0.01);

Y is a metal (other than manganese). For example, Y, if present, is an alkali metal (e.g., Na, K or Li), an alkaline earth metal (e.g., Mg, Ca or Be), or any combination thereof;

x is about 1.8 to about 2.2 (e.g., about 1.9 to about 2.1, about 1.95 to about 2.05, or about 2); and y is 0 to about 0.2 (e.g., 0 to about 0.1, 0 to about 0.05 or 0 to about 0.01).

In one embodiment, the process comprises reacting a compound of the formula $MnX_2(dioxane)_z$ (wherein z is about 1 to about 2, such as about 1.3 to about 1.5) with an alkylating agent (e.g., an alkyl metal reagent, such as an alkyl alkali metal reagent (e.g., a compound of the formula $R_2Y$, where Y is Na, Li or K), an alkyl alkaline earth metal reagent (e.g., a compound of the formula $R_2Y$ or $RYX^1$, where Y is Be, Ca, Mg or Be and X and $X^1$ are each, independently, halide (e.g., Cl, Br or I, preferably Cl), or any combination thereof) in an organic solvent (e.g., an organic solvent comprising ether, such as $Et_2O$).

In one embodiment, the process comprises reacting a compound of the formula $MnX_2(dioxane)_z$ (wherein z is about 1 to about 2, such as about 1.3 to about 1.5) with an alkyl magnesium reagent of the formula $RMgX^1$, $R_2Mg$, or a combination thereof (wherein X and $X^1$ are each, independently, halide, e.g, Cl, Br or I, preferably Cl) in an organic solvent (e.g., an organic solvent comprising ether, such as $Et_2O$).

Without wishing to be bound by theory, the inventor theorizes that in one step, the dioxane acts to (i) help solubilize $MnCl_2$ in diethyl ether, (ii) drive the reaction to completion by precipitating out the magnesium salts, (iii) form more reactive $R_2Mg$, and (iv) reduce the amount of unwanted magnesium salts in the final product. Four equivalents of dioxane is optimal to precipitate all the magnesium halide salts formed during the reaction as $MgX_2(dioxane)_2$.

In one embodiment, the $MnX_2$ dioxane complex is formed by reacting $MnX_2$ with an excess (such as 4 equivalents) of dioxane to afford $MnX_2(dioxane)_z$. In another embodiment, $MnX_2$ is reacted with more than 4 equivalents of dioxane to form $MnX_2(dioxane)_z$ which is subsequently isolated, then (4-z) equivalents of dioxane are added to the $MnX_2(dioxane)_z$ complex before reaction with the alkyl magnesium reagent. In a preferred embodiment, $MnX_2$ is stirred with 4 equivalents of dioxane and the $MnX_2$ dioxane compound thus formed is reacted in situ with the alkyl magnesium reagent.

In one embodiment, the organic group R does not contain a β-hydrogen substituent (e.g., R is mesityl, neopentyl, trimethylsilylmethyl or benzyl). In a preferred embodiment, R is neopentyl or mesityl.

In one embodiment, y is 0. In one embodiment, n is 0. In one embodiment, R is neopentyl. In one embodiment, X is Cl. In one embodiment, $X^1$ is Cl. In one embodiment, the organic solvent is diethyl ether.

In one embodiment, Y is an alkali metal (e.g., lithium, sodium, potassium) or an alkaline earth metal (e.g., magnesium, calcium, beryllium).

In a preferred embodiment, R is neopentyl, X and $X^1$ are Cl, y is 0 and the organic solvent is diethyl ether. In a preferred embodiment, the alkyl magnesium reagent is neopentyl magnesium chloride.

Thus, in a preferred embodiment, the present invention relates to a process for preparing bis(neopentyl)manganese (e.g., bis(neopentyl)manganese free or substantially free of organic residue (solvent) and/or other metal (e.g., magnesium). The process comprises reacting $MnCl_2(dioxane)_{1.3-1.5}$ with (i) neopentyl magnesium chloride, (ii) bis(neopentyl)magnesium, or (iii) a combination thereof, in diethyl ether.

In another embodiment, the present invention relates to a manganese dialkyl, such as $MnR_2$ wherein R is an organic ligand that does not contain a β-hydrogen substituent (e.g., R is mesityl, neopentyl, trimethylsilylmethyl or benzyl, that is free or substantially free of metal ions (other than manganese, e.g., Mg, or Li). In another embodiment, the present invention relates to a manganese dialkyl, such as $MnR_2$ wherein R is an organic ligand that does not contain a β-hydrogen substituent (e.g., R is mesityl, neopentyl, trimethylsilylmethyl or benzyl, that is free or substantially free of organic residue (e.g., organic solvent used during the synthesis of the manganese dialkyl). In another embodiment, the present invention relates to a manganese dialkyl that is free or substantially free of metal ions (other than manganese, e.g., Mg, or Li) and free or substantially free of organic residue (e.g., organic solvent used during the synthesis of the manganese dialkyl).

In another embodiment, the present invention relates to a manganese dialkyl, such as $MnR_2$ wherein R is an organic ligand that does not contain a β-hydrogen substituent (e.g., R is mesityl, neopentyl, trimethylsilylmethyl or benzyl, containing less than about 2 wt %, such as less than about 1 wt %, less than about 0.5 wt %, less than about 0.1 wt %, less than about 0.05 wt %, less than about 0.01 wt %, less than about 0.005 wt % or less than about 0.001 wt % of a metal ion (e.g., Mg, or Li).

In another embodiment, the present invention relates to a manganese dialkyl, such as $MnR_2$ wherein R is an organic ligand that does not contain a β-hydrogen substituent (e.g., R is mesityl, neopentyl, trimethylsilylmethyl or benzyl, containing less than about 2 wt %, such as less than about 1 wt %, less than about 0.5 wt %, less than about 0.1 wt %, less than about 0.05 wt %, less than about 0.01 wt %, less than about 0.005 wt % or less than about 0.001 wt % of organic residue (e.g., organic solvent used during the synthesis of the manganese dialkyl)

In another aspect, the present invention relates to a process for preparing a metal hydride according to any of the embodiments described herein (e.g., a metal hydride suitable for use in hydrogen storage, e.g., a metal hydride of formula (I) or (II)). Thus, in a further embodiment, the present invention relates to a process for preparing a manganese hydride (e.g., a metal hydride of formula (I) or (II)) comprising hydrogenating a compound of formula (III).

For example, the process can involve (i) hydrogenating an dialkyl metal compound of Formula (III); (ii) applying a vacuum to the product of step (i); and optionally, (iii) hydrogenating the product obtained in step (ii); and (iv) applying a vacuum to the product of step (iii).

In one embodiment, step (i) further comprises isolating the hydrogenated product (e.g., by filtration) prior to step (ii).

In one embodiment, the hydrogenation in step (i) is conducted at a hydrogen pressure of between about 1 bar and about 200 bar, such as between about 1 bar and about 150 bar, about 1 bar and about 125 bar or about 1 bar and about 100 bar. In additional embodiments, the hydrogenation in step (i) is conducted at a hydrogen pressure of about 1 bar, about 5 bar, about 10 bar, about 15 bar, about 20 bar, about 25 bar, about 30 bar, about 40 bar, about 50 bar, about 60 bar, about 70 bar, about 80 bar, about 90 bar, or about 100 bar.

In one embodiment, step (i) is conducted at a temperature of from about 15° C. to about 200° C., such as from about 15° C. to about 100° C., from about 20° C. to about 50° C., from about ambient temperature (e.g., from about 25° C.) to about 40° C., or from about 20° C. to about 30° C. In one embodiment, step (i) is conducted at ambient temperature. In one embodiment, step (i) is conducted at ambient temperature followed by 100° C.

In one embodiment, step (i) is conducted in the absence of solvent.

In another embodiment, step (i) is conducted in an organic solvent (e.g., an aromatic or non-aromatic organic solvent). In one embodiment, step (i) is conducted in a solvent selected from toluene and tetrahydrofuran. In one embodiment, step (i) is conducted in a dialkylether solvent, such as diethyl ether. In one embodiment, step (i) is conducted in an aromatic solvent, such as toluene. In one embodiment, step (i) is conducted in an aliphatic solvent such as a hydrocarbon solvent e.g., pentane, hexane, heptane, octane, and combinations thereof. In one embodiment, step (i) is conducted in a solvent selected from toluene, diethyl ether, petroleum ether, and combinations thereof. In one embodiment, the solvent is petroleum ether. Preferably, the solvent in step (i) is anhydrous.

In another embodiment, step (i) is conducted in an organic solvent (e.g., an aromatic or non-aromatic organic solvent) followed by further hydrogenation in the absence of an organic solvent.

In a further embodiment, step (i) also comprises hydrogenating a metal alkyl (e.g., $M^2R$, wherein R is an alkyl group, such as an R group described in any embodiment above, and $M^2$ is a metal other than manganese (e.g., iron)). In this embodiment, a mixed manganese/$M^2$ hydride may be produced.

In one embodiment, step (ii) is conducted at a temperature of from about 20° C. to about 250° C., such as from about 25° C. to about 200° C. or from about 25° C. to about 150° C. In one embodiment, step (ii) is conducted at about 25° C. In another embodiment, step (ii) is conducted at about 50° C. In a further embodiment, step (ii) is conducted at about 100° C. In yet another embodiment, step (ii) is conducted at about 150° C. In yet another embodiment, step (ii) is conducted between about 100° C. and about 150° C.

In one embodiment, step (ii) is performed for a period of time from about 1 to about 48 hours, such as from about 1 to about 24 hours, from about 1 to about 10 hours, from about 2 to about 10 hours, e.g., for about 4 hours or about 8 hours.

In one embodiment, step (iii) is conducted at a temperature of from about 20° C. (e.g., ambient temperature or about 25° C.) and about 250° C., such as from about 50° C. to about 200° C., from about 100° C. to about 200° C. or from about 150° C. to about 200° C. In one embodiment, step (iii) is conducted at about 150° C. In another embodiment, step (iii) is conducted at about 180° C.

In one embodiment, step (iii) is performed for a period of time from about 1 to about 10 hours, such as from about 2 to about 10 hours or from about 2 to about 6 hours, e.g., for about 2 hours or for about 6 hours.

In one embodiment, the hydrogenation in step (iii) is conducted at a hydrogen pressure of between about 1 bar and about 200 bar, such as between about 50 bar and about 170 bar, between about 100 bar and about 150 bar or between about 120 bar and about 150 bar. In additional embodiments, the hydrogenation in step (i) is conducted at a hydrogen pressure of about 1 bar, about 5 bar, about 10 bar, about 15 bar, about 20 bar, about 25 bar, about 30 bar, about 40 bar, about 50 bar, about 60 bar, about 70 bar, about 80 bar, about 90 bar, about 100 bar, about 120 bar or about 150 bar.

In one embodiment, step (iii) is conducted in the absence of solvent.

In another embodiment, step (iii) is conducted in an organic solvent (e.g., an aromatic or non-aromatic organic solvent). In one embodiment, step (iii) is conducted in a solvent selected from toluene and tetrahydrofuran. In one embodiment, step (iii) is conducted in a dialkylether solvent, such as diethyl ether. In one embodiment, step (iii) is conducted in an aromatic solvent, such as toluene. In one embodiment, step (iii) is conducted in an aliphatic solvent such as a hydrocarbon solvent e.g., pentane, hexane, heptane, octane, and combinations thereof. In one embodiment, step (i) is conducted in a solvent selected from toluene, diethyl ether, petroleum ether, and combinations thereof. Preferably, the solvent in step (iii) is anhydrous.

In one embodiment, step (iv) is conducted at a temperature of from about 20° C. (e.g., ambient temperature or about 25° C.) to about 250° C., such as from about 50° C. to about 200° C., from about 100° C. to about 200° C. or from about 150° C. to about 200° C. In one embodiment, step (iv) is conducted at about 150° C.

In one embodiment, step (iv) is performed for a period of time from about 1 to about 10 hours, such as from about 2 to about 10 hours or from about 2 to about 6 hours, e.g., for about 2 hours or about 6 hours.

In a preferred embodiment, the process comprises steps (i)-(iv) (i.e., step (iii) and (iv) are not optional and form part of the process).

In another embodiment, the process further comprises (v), subjecting the product of step (iv) to one or more (such as about 5 or more, about 10 or more, about 20 or more, about 30 or more, about 40 or more or about 50 or more) additional hydrogen adsorption-desorption cycles.

In another embodiment, the present invention relates to a process for purifying a metal hydride (e.g., a manganese hydride of formula (I) or (II)). The process comprises subjecting the metal hydride (e.g., a manganese hydride of formula (I) or (II)) to one or more (such as about 5 or more, about 10 or more, about 20 or more, about 30 or more, about 40 or more or about 50 or more) hydrogen adsorption-desorption cycles.

In one embodiment, hydrogen adsorption-desorption cycles may be conducted at a hydrogen pressure of between about 1 bar and about 200 bar, such as between about 50 bar and about 170 bar, between about 100 bar and about 150 bar or between about 120 bar and about 150 bar. In additional embodiments, the hydrogenation in step (i) is conducted at a hydrogen pressure of about 1 bar, about 5 bar, about 10 bar, about 15 bar, about 20 bar, about 25 bar, about 30 bar, about 40 bar, about 50 bar, about 60 bar, about 70 bar, about 80 bar, about 90 bar, about 100 bar, about 120 bar or about 150 bar Hydrogen Storage In another embodiment, the present invention relates to a method of storing hydrogen, the method comprising:
  providing a metal hydride according to any of the embodiments described herein (e.g., a metal hydride of formula (I)) or (II);
  adding hydrogen to the metal hydride; and
  allowing the hydrogen to coordinate to (e.g., be absorbed by) the metal hydride.

In another embodiment, the present invention relates to a method of storing hydrogen in a storage system, the method comprising:
  providing a metal hydride according to any of the embodiments described herein (e.g., a metal hydride of formula (I) or (II)) in a system;
  adding hydrogen to the metal hydride in the storage system; and
  allowing the hydrogen to coordinate to (e.g., be absorbed by) the metal hydride in the storage system.

In one embodiment, the hydride is compacted into a pellet form, optionally with a binder and/or lubricant (e.g., amorphous carbon, paraffin, mineral oil, or a polymer such as cellulose or polypropylene) or other material (e.g., an inorganic compound such as $TiO_2$, a metal or a metal alloy such as Ni to facilitate the pelletization process). The binder, lubricant and/or other material may be incorporated at this stage to minimize the effects of poisoning, hydrolysis or other potentially adverse reaction induced by contaminants in the hydrogen supply to the material in its final form. Additional additives (e.g., porous carbons, metal organic frameworks (MOFs) and covalent organic frameworks (COFs)) may also be added to accelerate the rate at which the hydrogen is adsorbed and desorbed by the metal hydrides described herein. In one embodiment, the hydride is deposited in the macropores of a honeycomb structured support.

In one embodiment, the storage system is a hydrogen storage tank with the metal hydride in the storage tank. The storage tank may comprise one or more openings in a wall of the storage tank. Fluids, such as hydrogen gas, can pass into and out of the storage tank through the one or more openings. The system may further comprise one or more valves which control the passage of fluids through the one or more openings. The one or more valves can be used to release pressure inside the storage tank by opening said one or more valves and allowing fluids to pass out of the storage tank through the one or more openings. The system may also further comprise a compressor (e.g., a gas compressor) for adding hydrogen into the storage tank.

In additional embodiments, the method of storing hydrogen further comprises releasing the hydrogen from the metal hydride (e.g., a metal hydride in a storage system). In one embodiment, the hydrogen is released from the metal hydride by reducing the pressure of the hydrogen in the storage system. In one embodiment, the hydrogen is released from the metal hydride by changing (e.g., increasing) the temperature of the storage system.

Yet another embodiment of the present invention relates to a hydrogen storage system comprising a storage system and a metal hydride within the storage system, wherein the metal hydride is encompassed by any of the embodiments described herein (e.g., a metal hydride of formula (I)).

The metal hydrides of the present invention may be useful in other applications, such as, but not limited to, methane adsorption, compressed natural gas storage, propellants, battery technologies, sorbents, olefin polymerization catalysts and sensors. The metal hydrides of the present invention may also be useful in other applications, such as, but not limited to, propelling electric and/or hybrid vehicles, and storing electricity while connected to the electrical grid. In one embodiment, the present invention relates to a storage system (which can be of any size and be stationary or mobile) for producing energy in conjunction with a fuel-cell or heat using an oxidant, the system comprising a metal hydride according to any embodiment described herein within the storage system.

A propellant is a material that is used to move or propel an object, such as a jet or rocket. A propellant may comprise a fuel and an oxidizer. The fuel may be, for example, gasoline, jet fuel or rocket fuel. When the metal hydrides of the present invention are used in a propellant, the propellant further comprises hydrogen. The hydrogen may coordinate to a metal center present in the metal hydride of the present invention. In one embodiment, the hydrogen is in liquid form. In a preferred embodiment, the propellant further comprises an oxidizer, for example, liquid oxygen. In one embodiment, the propellant is used to propel a jet or a rocket, In another embodiment, it is used in conjunction with an oxidixer in a flame-producing device such as, e.g., a welding torch.

A battery comprises one or more electrochemical cells, which convert stored chemical energy into electrical energy. The metal hydrides of the present invention may be used to coordinate to and store a compound in a battery. In a preferred embodiment, the compound that is stored is hydrogen. In one embodiment, the battery converts energy stored in the hydrogen into electrical energy. In one embodiment, the metal hydrides of the present invention are used in conjunction with a fuel cell for generating electricity.

A sorbent is a material that is used to absorb a liquid or a gas. The metal hydrides of the present invention may be used as a sorbent to absorb a liquid or a gas. For example, the metal hydrides of the present invention may be used to absorb hydrogen. In one embodiment, the hydrogen is liquid form. In another embodiment, the hydrogen is in the form of a gas.

Another embodiment is a catalyst system for polymerization of olefins comprising a metal hydride of the present invention. The catalyst system may further comprise a support.

Yet another embodiment is a process comprising polymerizing or copolymerizing olefins (e.g., ethylene, propylene) carried out in the presence of a catalyst system of the present invention.

A sensor is used to detect a substance or to measure a physical quantity. The sensor gives a signal that the substance has been detected or gives a signal representing the measurement of the physical quantity. The signal can be read by an observer or by an instrument.

The metal hydrides of the present invention may be used in a sensor. For example, the metal hydrides of the present invention may be used to detect hydrogen, e.g., in a system. In one embodiment, the metal hydrides of the present invention measure the amount of hydrogen that is present in a system. In one embodiment, the hydrogen is in liquid form. In another embodiment, the hydrogen is in the form of a gas.

DETAILED DESCRIPTION OF THE INVENTION

Definitions

Figure 1:
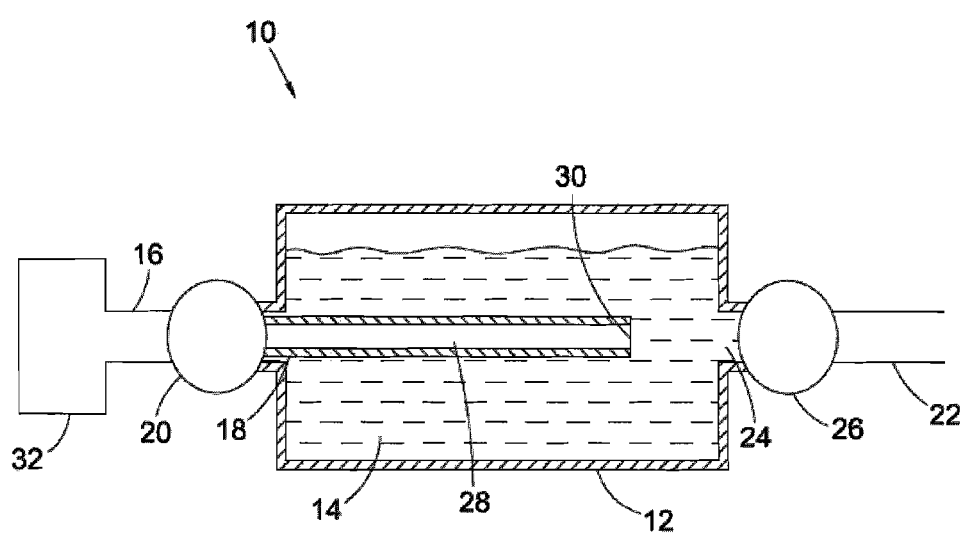
FIG. 1 depicts an embodiment of a storage system useful in the present invention.

Unless defined otherwise, all technical and scientific terms used herein generally have the same meaning as commonly understood by one of ordinary skill in the art to which this invention belongs.

The term "comprising" is open ended and, in connection with a composition, refers to the elements recited. The term "comprising" as used in connection with the compositions described herein can alternatively cover compositions "consisting essentially of" or "consisting of" the recited components.

The term "coordinate" as used here is not limited to a specific type of interaction between a metal center and hydrogen. For example, in one embodiment, the interaction between a metal center and hydrogen is a Kubas interaction.

The term "Kubas interaction" refers to hydrogen bound in a non-dissociative manner as a dihydrogen molecule to a transition metal center. In a Kubas interaction, free d-electrons of a metal centre interact with hydrogen. Specifically, where the metal centre has a low coordination number, the dihydrogen shares both of its σ-bonding electrons with the metal centre, and the metal centre back donates electrons by overlap of its π symmetry d-orbital with the empty antibonding σ* empty orbital of the dihydrogen. This results in a lengthening of the H—H bond (without rupture) and a shift to a lower wavenumber for the H—H resonance (see, e.g. *J. Am. Chem. Soc.*, 119, 9179-9190, 1997).

Without wishing to be bound by theory, the inventor theorizes that one or more $H_2$ molecules interact with the manganese centers by Kubas interactions to form maganese hydrides of the formula $MnH_x$ in which x is about 4, about 6, about 8 or about 10. However, bimolecular and/or free radical processes may also occur leading to maganese hydrides of the formula $MnH_x$ in which x is about 3, about 5 about 7 or about 9.

The term "substantially free" as used here in means containing less than about 2 wt %, such as less than about 1 wt %, less than about 0.5 wt %, less than about 0.1 wt %, less than about 0.05 wt %, less than about 0.01 wt %, less than about 0.005 wt % or less than about 0.001 wt % of a specified element or compound.

The term "organic group" refers to any carbon containing group that may be present in a metal alkyl of Formula (III), or in a metal hydride of Formulas (I) and (II) following hydrogenation of the metal alkyl of Formula (III). For example, the organic group may be a solvent used in the formation of the metal alkyl or metal hydride that has not been fully removed during the synthesis process (e.g., diethyl ether). Another example of an organic ligand may be a ligand (e.g., trimethylsilylmethyl, mesityl, neopentyl or benzyl) that is not fully removed from the metal center during formation of the metal hydride. The organic ligand may also be a compound (e.g., a protic compound, such as methanol) that is added to the metal hydride in order to increase microporosity of the metal hydride structure (e.g., by forming bridging methoxide ligands within the structure), thereby facilitating $H_2$ moving in and out of the metal hydride.

As used herein, the term "alkyl" refers to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include, e.g., methyl, ethyl, n-propyl, n-butyl, n-pentyl, and n-hexyl. Representative saturated branched alkyl groups include, e.g., isopropyl, sec-butyl, isobutyl, tert-butyl, neopentyl, and isopentyl. In a preferred embodiment, an "alkyl" group does not contain a β-hydrogen substituent.

As used herein, the term "aryl" refers to an aromatic hydrocarbon (mono- or multi-cyclic) having from 6 to 24 carbon atoms (e.g., phenyl, naphthyl), bound to the metal center via a metal-carbon bond.

As used herein, the term "arylalkyl" refers to an alkyl-aryl group, wherein alkyl and aryl are as defined herein (e.g., benzyl).

As used herein, the term "heteroararyl" refers to an aromatic group (mono- or multi-cyclic) having from 5 to 24 carbon atoms, additionally containing one or more N, S or O atoms.

One of ordinary skill in the art will readily understand that a metal hydride having a non-integral stoichiometry, such as $MnH_{4.2}$, refers to a material having manganese atoms coordinated with varying amounts of hydrogen (e.g., an average of 9 parts $MnH_4$ to 1 part $MnH_6$). Additionally, any metal hydride defined herein having an integral stoichiometry of metal to hydride ligand (e.g., $MnH_x$) is intended to also cover a metal hydride sample having an overall mixed stoichiometry of $MnH_{(x-0.2\ to\ x+0.2)}$ (e.g., $MnH_{3.8-4.2}$ or $MnH_{5.8-6.2}$, for $MnH_4$, $MnH_6$, respectively).

Metal Hydrides

In one embodiment, any of the metal hydrides described herein has a BET surface area of less than about 5 $m^2/g$, such as less than about 4 $m^2/g$, such as less than about 3 $m^2/g$, less than about 2 $m^2/g$ or less than about 1.5 $m^2/g$, such as about 1.4 $m^2/g$.

In another embodiment, the metal hydride described herein has a BET surface area of about 2 $m^2/g$ or greater, such as about 5 $m^2/g$ or greater, about 7.5 $m^2/g$ or greater, about 10 $m^2/g$ or greater, about 25 $m^2/g$ or greater, about 50 $m^2/g$ or greater, about 75 $m^2/g$ or greater, about 100 $m^2/g$ or greater, about 150 $m^2/g$ or greater, about 200 $m^2/g$ or greater, about 250 $m^2/g$ or greater, about 275 $m^2/g$ or greater, about 300 $m^2/g$ or greater, about 350 $m^2/g$ or greater, about 400 $m^2/g$ or greater, about 450 $m^2/g$ or greater or about 500 $m^2/g$ or greater.

In other embodiments, the BET surface area is from about 2 $m^2/g$ to about 1000 $m^2/g$, such as from about 10 $m^2/g$ to about 750 $m^2/g$, from about 50 $m^2/g$ to about 500 $m^2/g$, from about 100 $m^2/g$ to about 500 $m^2/g$, from about 250 $m^2/g$ to about 500 $m^2/g$, from about 300 $m^2/g$ to about 500 $m^2/g$, or from about 300 $m^2/g$ to about 400 $m^2/g$.

In one embodiment, the metal hydride is of Formula (I) and x is about 1.5 to about 10. In another embodiment, x is about 2 to about 10. In another embodiment, x is about 4 to about 10. In another embodiment, x is about 6 to about 10. In another embodiment, x is about 8 to about 10. In another embodiment, x is about 1.8 to about 2.2, e.g., about 2. In a further embodiment, x is about 3.8 to about 4.2, e.g., about 4. In a further embodiment, x is about 5.8 to about 6.2, e.g., about 6. In a further embodiment, x is about 7.8 to about 8.2, e.g., about 8. In a further embodiment, x is about 9.8 to about 10.2, e.g., about 10. In a further embodiment, x is about 2.8 to about 3.2, e.g., about 3. In a further embodiment, x is about 4.8 to about 5.2, e.g., about 5. In a further embodiment, x is about 6.8 to about 7.2, e.g., about 7. In a further embodiment, x is about 8.8 to about 9.2, e.g., about 9.

In one embodiment, the metal hydride is of Formula (II) and x is about 1.8 to about 2.2. In another embodiment, x is about 1.9 to about 2.1. In another embodiment, x is about 2. In another embodiment, x is about 0.1 to about 2.2.

In one embodiment, the metal hydrides described herein are amorphous or substantially amorphous (e.g., with little (e.g., nanoscopic order) or no long range order in the position of the atoms in the hydride structure). In one embodiment, the metal hydrides described herein are in the form of a gel.

In one embodiment, the metal hydrides described herein are mesoporous (e.g., have a pore diameter between about 2 and about 50 nm). In another embodiment, the metal hydrides described herein are microporous (e.g., have a pore diameter less than about 2 nm, such as less than about 1 nm).

In further embodiments, the metal hydrides described herein exhibit a gravimetric hydrogen absorption at least about 2%, at least about 3%, at least about 4%, at least about 5%, at least about 6%, at least about 7%, at least about 8%, at least about 9%, at least about 10%, at least about 11%, at least about 12%, at least about 13% or at least about 14%, e.g., in an amount up to about 14%, such as from about 2.0% to about 14.0%, from about 8.0% to about 12.0%, or about 3.5%, about 7.0%, about 10.5%, about 14%) based upon 100% total weight of the metal hydride without molecular hydrogen stored in it.

In one embodiment of the metal hydrides described herein, when x is greater than about 2 (e.g., greater than about 3.8), the material is at a pressure of about 10 bar or more of hydrogen (e.g., at about 15 bar, at about 20 bar, at about 25 bar, at about 30 bar, at about 40 bar, at about 50 bar, at about 75 bar, at about 85 bar, about 100, about 125 or about 150 bar of hydrogen, or higher).

Synthesis of Dialkyl Manganese Compounds and Manganese Hydrides

The inventor has surprisingly found that transition metal dialkyl complexes (e.g., manganese dialkyl complexes, such as bis(neopentyl)manganese) may be prepared in high yield and high purity via a one step reaction of a metal halide dioxane complex (e.g., $MnCl_2(dioxane)_{1.3-1.5}$) with an alkyl Grignard (e.g., (neopentyl)magnesium chloride), a dialkyl magnesium reagent (e.g., bis(neopentyl)magnesium), or, a combination thereof, in an ether solvent (e.g., diethyl ether). In one embodiment, the reaction is conducted in the presence of excess dioxane. For example, $MnCl_2(dioxane)_{1.3-1.5}$ may be prepared by reaction of $MgCl_2$ with an excess (e.g., about 4 equivalents) of dioxane. The excess dioxane may be present during reaction of the $MnCl_2(dioxane)_{1.3-1.5}$ with the Grignard and/or dialkyl magnesium reagent.

Hydrogenation of the resulting metal dialkyl complexes (such as bis(neopentyl)manganese) affords transition metal hydride frameworks, such as compounds of Formula (I) and (II) that interact with hydrogen to form solid state hydrides (such as the hydrides $MnH_x$, wherein x is about 2.8 to about 10 (or about 3.8 to about 10), e.g., x is about 2.8 to about 3.2, about 3.8 to about 4.2, about 4.8 to about 5.2, about 5.8 to about 6.2, about 6.8 to about 7.2, about 7.8 to about 8.2, about 8.2 to about 9.2 or about 9.8 to about 10.2, e.g., $MnH_3$, $MnH_4$, $MnH_5$, $MnH_6$, $MnH_7$, $MnH_8$, $MnH_9$ or $MnH_{10}$ (for further example, x is about 3.8 to about 4.2, about 5.8 to about 6.2, about 7.8 to about 8.2, or about 9.8 to about 10.2, such as, e.g., $MnH_4$, $MnH_6$, $MnH_8$, $MnH_{10}$) and can reversibly release hydrogen, thereby acting as materials for hydrogen storage.

Typically, organomanganese (II) compounds may be prepared by trans-metalation of a manganese dihalide with an organolithium or organomagnesium reagent (see, e.g., Cahiezet et al., *J. Chem. Rev.*, 109, 1434-1476, 2009). To prepare bis(alkyl)manganese (II) compounds on an industrial scale, $MnCl_2$ is typically used as it is cheaper than both $MnBr_2$ and $MnI_2$. However, $MnCl_2$ is the least soluble of the three dihalides in organic solvents and reacts slowly with Grignard reagents.

The synthesis of bis(mesityl)manganese has previously been reported in 50% yield by reaction of $MnCl_2$ with mesityl magnesiumbromide in tetrahydrofuran (THF) (see, e.g., Gambarotta et al., *J. Chem. Soc., Chem. Commun.*, 1128, 1983; Fischer et al., *J. Organomet. Chem.*, 694, 1107-1111, 2009). The THF solvent helps to solubilise the $MnCl_2$, which aids the reaction with mesityl magnesiumbromide. The present inventor, however, has found that THF coordinates to the dialkyl manganese product, thereby making it difficult to isolate the base free dialkyl product. Coordinated THF carries through to the final manganese hydride product prepared from bis(mesityl)manganese prepared according to Gambarotta, adversely affecting the hydrogen adsorption properties (i.e., gravimetric $H_2$ wt % performance).

Chloro-Grignard reagents are preferred Grignard reagents for industrial scale synthesis, due their lower cost compared to corresponding bromo-Grignard reagent. In both cases, however, removal of $MgX_2$ (X=Cl, Br) from the final manganese dialkyl product is difficult because of the solubility of these magnesium halide salts in ether and the formation of magnesium etherates. However, if the reaction mixture containing the dialkyl manganese product, the magnesium halide (e.g., $MgCl_2$) and diethyl ether is heated in vacuo in order to remove the ether and form free magnesium halide, this leads to complexation of the Lewis acidic magnesium halide to the dialkyl manganese product, rendering the organometallic insoluble in hydrocarbon solvents. Because of these problems, dioxane may be used to remove magnesium halide from the final product by forming an insoluble bis(dioxane) adduct of the magnesium halide. For this reason, addition of dioxane after completion of the dialkylation reaction is desirable. If more than 2 equivalents of dioxane are used, however, the dioxane, like THF, can coordinate to the final manganese dialkyl product, and is difficult to remove.

Organomagnesium reagents of the type $(alkyl)_2Mg$ react faster than the corresponding Grignard reagent. For example, the synthesis of bis[(trimethylsilyl)methyl]manganese(II) was reported in ca. 80% yield by reaction of $MnCl_2$ with bis(trimethylsilylmethyl)magnesium in diethylether after three days stirring at 298 K (see, e.g., Alberola et al., *Organometallics*, 28, 2112-2118, 2009). Preparation of $(alkyl)_2Mg$ or $Mg(aryl)_2$ reagents, however, requires manipulation of the Schlenk equilibrium by adding dioxane to the alkyl or aryl magnesium halide (e.g., RMgX wherein R=alkyl or aryl and X=Cl, Br, I) in a prior step, which causes precipitation of magnesium halide, leaving the $(alkyl)_2Mg$ reagent in solution. This adds an undesirable and costly step to any synthetic procedure carried out on an industrial scale, and does not remove the magnesium halide by-product from the final reaction mixture, making it necessary to add dioxane a second time.

Bis(neopentyl)manganese and bis[(trimethylsilyl)methyl]manganese(II) have also been synthesized by Wilkinson by reacting a 1:1 mixture of the Grignard and $(alkyl)_2Mg$ reagent in diethyl ether with $MnCl_2$ in 30-50% yield (see, e.g., Andersen et al., *J. Chem. Soc. Dalton Trans.*, 2204-2211, 1976; Andersen et al., *J. Chem. Soc., Chem. Commun.*, 1807-1808, 1985).

In order to circumvent the problems observed using Grignard (RMgX) reagents, more reactive alkyl lithium compounds (RLi) have also been used. This is unattractive, not only in terms of the higher cost of RLi over RMgX, but also because of the slow reaction of RLi with $MnX_2$ (X=Cl, Br) due to (i) the insolubility of these halides in ether, and (ii) the preferred formation of the "ate" complexes $R_3MnLi$ and $R_4MnLi_2$, which when hydrogenated downstream, lead to poorly performing hydrogen storage materials due to contamination by lithium and lithium etherates.

To overcome the low solubility of $MnBr_2$ in ether, Cahiez has reported that $MnBr_2$ may be solubilized with LiBr to form the complex, $MnBr_2$:LiBr (see, e.g., Cahiez et al., Tetrahedron Letters 30, 3545-3546, 1989). When following this procedure, however, the present inventor found that use of organolithium reagents led, in each case, to formation of the species $R_2MnBrLi$. It was not possible to remove the coordinated Li halide from the manganese alkyl, thereby leading to poorly performing hydrogen storage materials. $MnI_2$ reacts more rapidly with organolithium reagents because of its greater solubility in ether, but there are problems with LiI contaminating the final product due to the high solubility of LiI in ether and the solubility of LiI ether complexes in petroleum (see, e.g., Cahiez et al., J. Chem. Rev., 109, 1434-1476, 2009; Cahiez et al., Synthesis, 130-133, 1977; Cahiez et al., Synthesis, 37-40, 1984; Bartlett et al., Organometallics, 7, 1801-1806, 1988). Again, LiI is thus carried forward into the hydrogenated metal hydride product.

In order to take advantage of (i) the affinity of dioxane for Magnesium halides and (ii) the use of dioxane to accelerate reactions of Grignard reagents by forming more reactive $(alkyl)_2Mg$ or $Mg(aryl)_2$ species, while (iii) overcoming the insolubility of $MnCl_2$ in ether, the present inventor has employed a manganese dioxane complex (e.g., $MnCl_2$(dioxane)$_{1.3-1.5}$) for the first time as a starting material in the synthesis of dialkyl manganese complexes.

In the present inventor's adaptation of Wilkinson's synthesis (see, e.g., Andersen et al., J. Chem. Soc. Dalton Trans., 2204-2211, 1976; Andersen et al., J. Chem. Soc., Chem. Commun., 1807-1808, 1985), the soluble manganese dioxane complex reacts smoothly in ether to form the manganese bisalkyl product quantitatively and in high purity, with the insoluble magnesium chloride dioxane complex as the only other product. This is easily removed by filtration. In one step, dioxane therefore acts to (i) help solublize $MnCl_2$ in diethyl ether, (ii) drive the reaction to completion by precipitating out the magnesium salts, (iii) form more reactive $R_2Mg$, and (iv) reduce the amount of unwanted magnesium salts in the final product.

Without wishing to be bound by theory, the present inventor believes that the dioxane preferentially forms an insoluble complex with $MgCl_2$ over $MnCl_2$, thereby helping to drive the reaction to completion and remove the Magnesium salts from solution (see, e.g., Fowles et al., J. Chem. Soc. A, 1842-1846, 1968). For example, $MnCl_2$ may be reacted with 4 equivalents of dioxane followed by 2 equivalents of neopentyl magnesium chloride. The reaction mixture may be filtered and washed (e.g., with diethyl ether) and the filtrate removed in vacuo down to afford a quantitative yield of magnesium free (or substantially free) bis(neopentyl)Mn. This provides a simple one-step route to synthesizing dialkyl manganese complexes in high yield that are free (or substantially free) of impurities without the need for multiple extractions and purification procedures. The present inventor has found that that hydrogenation of $Mn(alkyl)_2$ or $Mn(aryl)_2$ complexes prepared according to the present invention affords metal hydrides that exhibit significantly better hydrogen storage capability when compared to metal hydrides prepared from $Mn(alkyl)_2$ or $Mn(aryl)_2$ complexes contaminated with lithium halides, solvents such as THF, magnesium halides (and solvates thereof such as magnesium halide etherates), $MnR_3^-$ and $MnR_4^{2-}$.

Thus, in one embodiment, the present invention relates to a process for preparing a manganese alkyl compound of the formula (III)

$$MnR_xY_yL_n \qquad (III)$$

wherein

R is an organic group (e.g., an organic alkyl group without a β-hydrogen substituent, such as mesityl, neopentyl, trimethylsilylmethyl or benzyl);

L is a Lewis base (e.g., an organic solvent (such as an ether solvent, e.g. $Et_2O$, dioxane, THF), water, $H_2S$, an amine, a phosphine, a sulfide, and combinations thereof);

n is 0 to about 1 (e.g., about 0 to about 0.8, 0 to about 0.6, 0 to about 0.5, 0 to about 0.4, 0 to about 0.2, about 0 to about 0.1, about 0 to about 0.05 or about 0 to about 0.01);

Y is a metal (other than manganese) (e.g., Y, if present, is an alkali metal (e.g., Na, K or Li), an alkaline earth metal (e.g., Mg, Ca or Be), or any combination thereof);

x is about 1.8 to about 2.2 (e.g., about 1.9 to about 2.1, about 1.95 to about 2.05, or about 2); and y is 0 to about 0.2 (e.g., 0 to about 0.1, 0 to about 0.05 or 0 to about 0.01).

The process comprises reacting a compound of the formula $MnX_2$(dioxane)$_z$ (wherein z is about 1 to about 2, such as about 1.3 to about 1.5) with an alkyl magnesium reagent of the formula $RMgX^1$, $R_2Mg$, or a combination thereof (wherein X and $X^1$ are each, independently, halide, e.g, Cl, Br or I, preferably Cl) in an organic solvent (e.g., an organic solvent comprising ether, such as $Et_2O$).

In one embodiment, the $MnX_2$ dioxane complex is formed by reacting $MnX_2$ with an excess (such as about 4 equivalents) of dioxane to afford $MnX_2$(dioxane)$_z$.

Preferred organic groups are neopentyl and mesityl. These groups are symmetrical and can easily be chlorinated to afford one product (e.g., neopentyl chloride). The neopentyl group contains no beta hydrogen, which is preferred in order to form a stable dialkyl manganese complex, and is relatively small and thus able to diffuse out of a solid structure more readily than larger alkyl groups. Trimethylsilylmethyl can also be used as the organic ligand.

In another embodiment, the present invention relates to a process for preparing a manganese hydride according to any of the embodiments described herein (e.g., a manganese hydride suitable for use in hydrogen storage). The process comprises (i) hydrogenating an dialkyl manganese compound (e.g., a compound of formula (III)); (ii) applying a vacuum to the product of step (i); and optionally, (iii) hydrogenating the product obtained in step (ii); and (iv) applying a vacuum to the product of step (iii).

In another embodiment, the process further comprises (v), subjecting the product of step (iv) to one or more (such as about 5 or more, about 10 or more, about 20 or more, about 30 or more, about 40 or more or about 50 or more) additional hydrogen adsorption-desorption cycles, for example, at between about 120 and 150 bar $H_2$.

In another embodiment, the present invention relates to a method of storing hydrogen comprising providing a metal hydride according to any of the embodiments described herein (e.g., a metal hydride of formula (I) or (II)), adding hydrogen to the metal hydride, and allowing the hydrogen to coordinate to the metal hydride. The storing of hydrogen may be carried out in a storage system.

One embodiment of a storage system suitable for hydrogen storage is a pressure vessel. For example, the pressure vessel may hold the metal hydride of the present invention at a temperature of up to 200° C., e.g., from about −100 to about 150° C., from about −50 to about 0° C., from about −25 to about 0° C., from about 0 to about 150° C., from about 0 to about 50° C., from about 10 to about 30° C. or from about 20 to about 25° C. In one embodiment, the storage system is substantially free of oxygen.

Hydrogen may be added to the storage system (e.g., a pressure vessel) and stored using the metal hydrides of the present invention. In one embodiment, no heating is required when adding hydrogen to the pressure vessel for storage.

The amount of hydrogen that can be stored by the metal hydrides of the present invention is proportional to the pressure in the storage system. For example, at higher pressures, more hydrogen can be stored by the metal hydrides of the present invention. The pressure in the storage system may be increased by adding hydrogen to the storage system. Without wishing to be bound by any particular theory, the inventor theorizes that as the pressure is increased, the number of Kubas interactions per metal centre may increase. For example, when the metal hydride is a manganese hydride such as $MnH_2$, one hydrogen molecule coordinated to the manganese (e.g., by a Kubas interaction) affords $MnH_4$. Two hydrogen molecules coordinated to the manganese (e.g., by Kubas interactions) affords $MnH_6$. Three hydrogen molecules coordinated to the manganese (e.g., by Kubas interactions) affords $MnH_8$. Four hydrogen molecules coordinated to the manganese (e.g., by Kubas interactions) affords $MnH_{10}$. As noted above, however, this process will appear continuous in the bulk state, resulting in the formation of a bulk material containing metal hydrides having a mixture of coordinated hydrogen molecules, and, therefore, an overall non-integer stoichiometry of manganese to hydrogen. Furthermore it may be possible (e.g., via a free radical and/or bimolecular process) to form molecular species of the formula $MnH_3$, $MnH_5$, $MnH_7$ and $MnH_9$.

In further embodiments, any of the metal hydrides described herein optionally contain one or more additional metals (e.g., a metal other than manganese). For example, the metal hydride may contain one or more additional metals selected from sodium, potassium, aluminum, beryllium, boron, calcium, lithium, magnesium and combinations thereof. In an alternate embodiment, the metal hydride may contain one or more additional metals (e.g., a metal other than manganese) wherein the one or more additional metals is a period 4, 5, 6, 7, 8, 9, 10, 11 and/or 12 transition metal, or a lanthanide, that forms a hydride upon treatment with hydrogen. For example, the metal hydride may contain one or more additional metals selected from zirconium, niobium, molybdenum, technetium, ruthenium, rhodium, palladium, silver, and combinations thereof. In one embodiment, any of the metal hydrides described herein may optionally contain one or more additional period 4, period 5 or period 6 transition metals. In another embodiment, the metal hydride may contain one or more additional metals selected from iron, zirconium, niobium, molybdenum, technetium, ruthenium, rhodium, palladium, silver, cadmium, hafnium, tantalum, tungsten, rhenium, osmium, iridium, platinum, gold, mercury, and combinations thereof. The one or more additional metals may be present in an amount of about 50 wt. % or less, about 40 wt. % or less, about 30 wt. % or less, about 25 wt. % or less, about 20 wt % or less, about 10 wt % or less, about 5 wt % or less, about 1 wt % or less, about 0.75 wt % or less, about 0.5 wt % or less, about 0.25 wt % or less, about 0.1 wt % or less, about 0.05 wt % or less or about 0.01 wt % or less. In one embodiment, the metal hydrides described herein contain no additional metal (e.g., no metal other than manganese).

The hydrogen pressure in the system may be increased using a compressor, such as a gas compressor, which pumps hydrogen into the system. Preferably, the hydrogen pressure in the system is increased to about 30 atm or more. For example, the hydrogen pressure in the system may be increased to from about 30 atm to about 500 atm, from about 50 atm to about 200 atm, or from about 75 atm to about 100 atm.

The system preferably has a temperature of (or operates at) up to 200° C., such as about −200° C. to 150° C. (e.g., about −100° C. to 150° C.), about −200° C. to 100° C., about 0° C. to 50° C., about 10° C. to 30° C., or about 20° C. to 25° C. In one embodiment, the system has a temperature (or operates at) about 25° C. to about 50° C. The system is preferably free of oxygen to prevent the oxidation of metal in the system. In one embodiment, the method of storing and releasing hydrogen in a system of the present invention may be carried out without adding heat to and/or cooling the system. In another embodiment, the method of storing and releasing hydrogen in a system of the present invention may be carried out by adding heat to and/or cooling the system.

In a further embodiment, the hydrogen is released from the storage system. For example, this may be accomplished by reducing the pressure of hydrogen in the system. In one embodiment, no heating is required in order to release the hydrogen from the metal hydride. For example, a valve in the storage system may be opened to allow hydrogen gas to escape from the system, thus decreasing the pressure in the storage system. In one embodiment, about 100% of the stored hydrogen is released. In additional embodiments, greater than about 50%, greater than about 55%, greater than about 60%, greater than about 70%, greater than about 75%, greater than about 80%, greater than about 90%, greater than about 95%, greater than about 97.5%, greater than about 99% or greater than about 99.5% of the hydrogen is released. The step of releasing the hydrogen pressure in the system may be carried out by allowing hydrogen gas to escape from the system, thus decreasing the hydrogen pressure. For instance, the step of releasing the hydrogen pressure may decrease the hydrogen pressure in the system to 100 atm or less (such as to 50 atm or less, 30 atm or less, or 20 atm or less). In another embodiment, the hydrogen is released from the storage system by increasing the temperature of the system.

Hydrogen may be added or released from the system at any point throughout the entire pressure gradient of the system without any adverse effects to the storage capacity of the system. In certain embodiments, hydrogen may be added or released from the system any number of times without any adverse effect to the storage capacity of the system. For example, the system can be filled with hydrogen and emptied of hydrogen at least 100, such as at least 200, at least 500, at least 1000 or at least 1500 times without a significant decrease in the storage capacity of the system.

In one embodiment, the storage system (e.g. pressure vessel) is a fuel tank in a vehicle, such as a truck or automobile.

Figure 2:
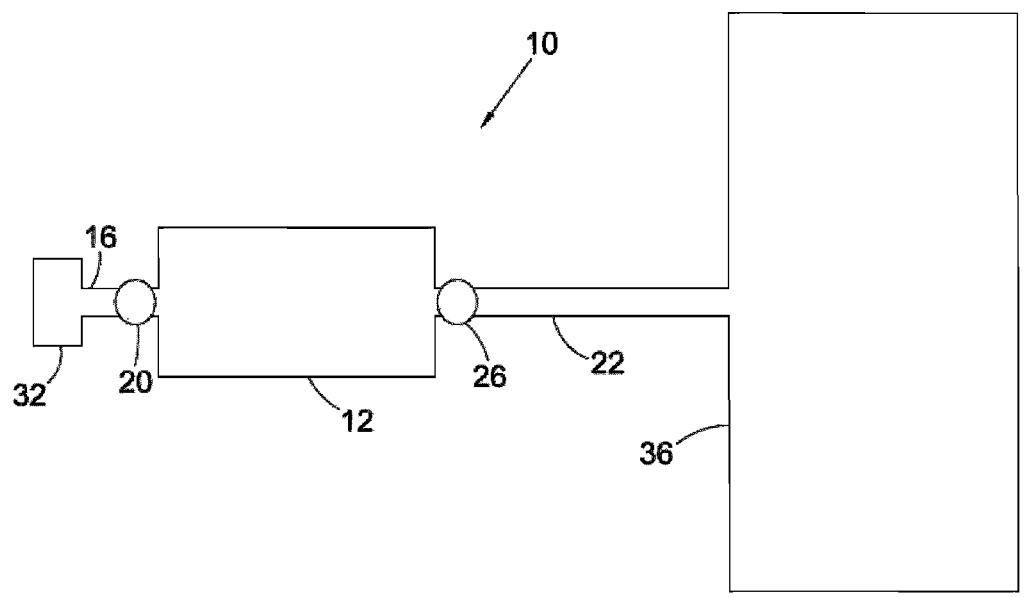
FIG. 2 depicts an embodiment of the storage system attached to a hydrogen fuel cell.

FIG. 1 depicts an embodiment of a storage system useful in the present invention. FIG. 2 depicts an embodiment of the storage system attached to a hydrogen fuel cell. The system 10 comprises a tank body 12 which is made of a material that is impermeable to hydrogen gas, thus preventing undesired leaking of the hydrogen gas out of the tank body 12. For example, the tank body 12 is made of metal, such as, e.g., steel or aluminum. Alternatively, the tank body 12 is made of a composite material, such as a composite of fibreglass and aramid. In another embodiment, the tank body 12 is made of a carbon fibre with a liner. The liner may be a polymer liner, such as a thermoplastic liner or a metal liner, such as a steel liner or an aluminum liner.

The metal hydride 14 of the present invention is present inside the tank body 12. In FIG. 1, the metal hydride 14 is in a gel form. The metal hydride 14 may partially fill or totally fill the tank body 12. In certain embodiments, the metal hydride may be present as a coating on a support or in pellet form, depending upon the requirements for pressure drops in the tank body. In additional embodiments, the metal hydride may be present in admixture with other compounds (such as a binder) which enhance the structural integrity and other properties of the coating or the pellet.

A first passage 16 leads to a first opening 18 in the wall of the tank body 12. A first valve 20 controls the flow of hydrogen gas through the first opening 18.

A second passage 22 extends from a second opening 24 in the wall of the tank body 12. A second valve 26 controls the flow of hydrogen gas through the second opening 24.

The first valve 20 and the second valve 26 can be any type of valve that controls the flow of hydrogen gas through the first opening 18 and the second opening 24, respectively. For example, the first valve 20 and the second valve 26 can be ball valves or gate valves.

In one embodiment, hydrogen is added to the system 10 as follows. A gas compressor 32 pumps hydrogen gas into the first passage 16. The first valve 20 is opened to allow the hydrogen gas to flow through the first opening 18 and into the tank body 12.

A passage tube 28 is in gaseous communication with the first opening 18 and extends into the interior of the tank body 12. The passage tube 28 facilitates the distribution of the hydrogen gas to the metal hydride 14. In one embodiment, the passage tube 28 is made of a material that is permeable to the hydrogen gas. This allows the hydrogen gas to pass through the wall of the passage tube 28 and into contact with the metal hydride 14. The passage tube is also preferably made of a material that is impermeable to the metal hydride 14, thus preventing the metal hydride 14 from entering into the interior of the passage tube 28. The passage tube 28 preferably opens into the interior of the tank body 12. The opening of the passage tube 28 is preferably covered with a filter 30 which prevents the metal hydride 14 from entering into the interior of the passage tube 28.

When the compressor 32 pumps hydrogen gas into the tank body 12, there is an increase of the hydrogen pressure inside the tank body 12. When the hydrogen pressure inside the tank body is increased, the metal hydride 14 is able to coordinate with a greater amount of hydrogen. Preferably, the increase in pressure causes an increase in the number of Kubas interactions per metal centre in the metal hydride 14. After the desired amount of hydrogen has been added to the system, the valve 20 is closed.

When desired, hydrogen may be released from the system 10 as follows. The second valve 26 is opened, which allows hydrogen gas to flow out of the tank body 12 through the second opening 24. When hydrogen gas flows out of the tank body through the second opening 24, there is a decrease in pressure inside the tank body 12. When the pressure is decreased inside the tank body 12, the metal hydride 14 releases hydrogen. For example, the decrease in pressure may cause a decrease in the number of Kubas interactions per metal centre of the metal hydride 14.

Hydrogen that is released by the metal hydride 14 can flow out of the tank body 12 through the second opening 24.

As shown in FIG. 2, the hydrogen can flow through the second passage 22 to a fuel cell 36. The fuel cell 36 preferably uses hydrogen as a fuel and oxygen as an oxidant to produce electricity. Typically, a filter is present at the second opening 24 in order to prevent loss of particulates downstream.

In an alternative embodiment, the storage system of the present invention comprises a storage tank with a single opening. In this embodiment, hydrogen flows both into and out of the storage tank through the single opening. A valve is used to control the flow of hydrogen through the opening. Since the enthalpies of $H_2$ binding are moderate to thermodynamically neutral and binding may be controlled by pressure, the tank may not need an exotic heat management system for most applications, unlike many prior hydrogen storage systems.

In one embodiment, the system is portable. As such, the system can be transported to a filling station to be filled with hydrogen. After being filled with hydrogen, the system can then be transported to a site where the hydrogen energy is to be used. Applications for this system include, but are not limited to, vehicles, airplanes, homes, buildings, and barbeques.

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

All chemicals were purchased from Sigma-Aldrich and used without further purification except for dry 40-60° C. petroleum ether, diethyl ether and toluene, which were purified via an MBraun Solvent Purification System which was dispensed inside the MBraun glovebox.

$MnCl_2(dioxane)_1$ was prepared according to Fowles et al., *J. Chem. Soc. A,* 1842-1846, 1968.

Nitrogen adsorption and desorption data were collected at 77K on a Micromeritics ASAP 2010™.

Infrared spectroscopy was conducted on a Perkin Elmer Spectrum RX1 using KBr discs. Approximately 5 mg of sample was ground with 200 mg IR grade, oven dried KBr and compressed to form a disc.

Hydrogen adsorption isotherms were obtained using a computer controlled gas sorption Sieverts apparatus manufactured by Hy-Energy. High purity hydrogen (Grade 6, 99.9999% purity) purchased from Air Liquide was used. Stainless steel spacers were added to the sample holder along with the material to reduce excess void space. The void space of the sample was calculated by performing a helium volume calibration at 298K using 3 each adsorption and desorption points (total of 6), with outlying values discarded and rerun. Excess hydrogen storage measurements on a 200 mg standard AX-21 sample (0.65 wt. % at 70 bar and 298 K) were performed and ensure correct functioning of the instrument and to ensure the accuracy of the isotherms. The reported gravimetric hydrogen storage capacity of Carbon-AX21 is 0.3 wt % at 35 bar (Bernard et al., *Assessment of Hydrogen Storage on Different Carbons*, IEA Report, 2001). This corresponds to 0.6 wt % at 70 bar which gives an error of ±0.07 wt % ((0.65−0.6)×100/70) at 100 bar $H_2$ with a 200 mg sample size. This sample size was chosen such that the absolute amount adsorbed was equivalent to that in our manganese hydride hydrogen storage experiments (ca. 1 mmol $H_2$) to eliminate systematic error, since the instrument measures total mols hydrogen adsorbed and then converts it to wt %.

True volumetric adsorption is defined as the amount of hydrogen adsorbed on or in a given volume of the solid portion of the sample. This may be calculated from the excess storage data and the skeletal density, thereby allowing a comparison between volumetric adsorption values of the solid phase alone from one sample to another without having to correct for the different textural void space in each material.

Example 1: Manganese Hydride Samples

Synthesis
1) Synthesis of $MnCl_2(dioxane)_{1.3-1.5}$

Dioxane (50 mL) was added to $MnCl_2$ (5.8 g, 46.7 mmol) and the mixture was stirred at room temperature overnight. The excess dioxane was removed in vacuo at $10^{-3}$ torr and the resulting solid was dried in vacuo ($10^{-3}$ torr) for 12 hours to afford $MnCl_2(dioxane)_{1.3-1.5}$ in quantitative yield. The Infra-red (IR) spectrum for the product exhibits C—H stretches at ~2800 $cm^{-1}$ and a characteristic coordinated ether C—O stretch between 1000 and 1100 $cm^{-1}$.

2) Synthesis of bis(neopentyl)manganese 240.30 for 1.3-213.95 for 1.0

$MnCl_2(dioxane)_1$ (10.0 g, 46.7 mmol) or $MnCl_2(dioxane)_{1.3}$ (11.22 g, 46.7 mmol) was suspended in 200 mL diethylether and enough dioxane was added to make the total amount of dioxane present to be four molar equivalents relative to $MnCl_2$ (12 mL, 140.1 mmol for $MnCl_2(dioxane)_1$; 10.8 mL, 126.1 mmol for $MnCl_2(dioxane)_{1.3}$) (or alternatively, $MnCl_2$ (5.8 g, 46.7 mmol) is stirred at 60° C. with 4 equivalents of dioxane (16 mL, 187 mmol) overnight, followed by cooling to room temperature and addition of 200 mL diethyl ether).

Neopentyl magnesium chloride (93.4 mmol) in 200 mL diethyl ether was then added dropwise and the resulting solution was stirred for 24 hours to give a pale orange suspension. The resulting white solid was then removed by filtration and washed with ether (2×50 mL) and the combined orange filtrates were concentrated in vacuo ($10^{-3}$ torr) to afford bis(neopentyl) manganese in 70% yield. Extraction of the resulting product into hexane followed by filtration and concentration in vacuo afforded bis(neopentyl)manganese in 50% yield that could be used without further purification.

The yield after hexane extraction for $Mesityl_2Mn$ synthesized from MesitylMgBr using the above procedure above was 30%. The yield after extraction into toluene and filtration for bis(trimethylsilylmethyl)manganese synthesized from trimethylsilylMgCl using the above procedure was 90%. It should be noted that these compounds are exceedingly air sensitive and that handling in the glove box even at 1 ppm $O_2$ in a solvated form for several hours can lead to oxidation, resulting in the appearance of a green color followed by a brick red color. See, e.g., Wilkinson et al., *J. Chem. Soc. Dalton Trans.*, 2204-2211, 1976. This oxidation may be followed by IR as oxidation leads to strong stretches observed at 800-1200 $cm^{-1}$ which are not present in the pure dialkyl. Care should be taken to avoid contamination with any coordinating solvents such as THF, water, amines, etc.

3) Alternate Synthesis of Bis(neopentyl)manganese $MnCl_2$ (10 g, 79.5 mmol) was stirred in 200 mL of diethyl ether to afford a pale pink suspension. To this a 1:1 mixture of neopentyl magnesium chloride and bis(neopentyl)magnesium dissolved in diethyl ether (total alkyl content 159 mmol) (see, e.g., Andersen et al., *J. Chem. Soc. Dalton Trans.*, 2204-2211, 1976) was added dropwise and the reaction was stirred for 24 hours at room temperature. All volatiles were removed in vacuo ($10^{-3}$ torr). The resulting solid was then extracted with warm (40° C.) petroleum ether and filtered to afford a white precipitate and a red-brown filtrate. Cooling the filtrate afforded red-brown crystals which were recrystallized twice from petroleum ether (−40° C.) to remove magnesium salts affording bis(neopentyl) manganese (4.7 g, 30% yield).

4) Preparation of Manganese (II) Hydride

Bis(neopentyl)manganese (75 mg, 0.38 mmol) was stirred in 100 mL of petroleum ether to afford a red-brown solution. The solution was transferred to a stainless steel PARR hydrogenation vessel, which was charged with 100 bar of $H_2$. The mixture was stirred for 24 hours at room temperature and then for a further 48 hours at 100 bar $H_2$ and 100° C. The resulting mixture was filtered and the resulting black precipitate was dried at 100° C. in vacuo ($10^{-3}$ torr) for 4 hours to afford a black air-moisture sensitive solid (Mnd-100) (42.8 mg). The material was further hydrogenated in the solid state using the PCT-Pro for four hours at 85 bar $H_2$ and 150° C. Following this, the sample was evacuated at 100° C. for two hours and then allowed to cool to room temperature to afford a black solid (Mnd-150-$H_2$-4 hrs) (21.5 mg).

Sample Characterization

Figure 3:
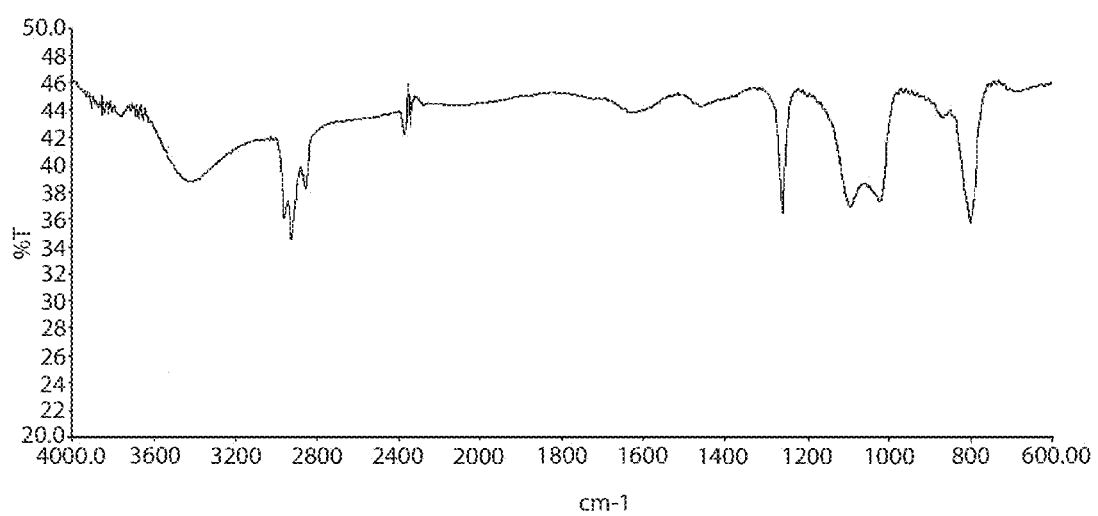
FIG. 3 depicts an IR spectrum of manganese hydride sample Mnd-100.

The Infra-red (IR) spectrum for sample Mnd-100 is shown in FIG. 3. Three C—H stretches are observed at 2852, 2925 and 2960 $cm^{-1}$, which correspond to a neopentyl ligand which has not been fully cleaved from the precursor compound via hydrogenolysis. A coordinated ether (C—O) stretch is observed at 1000-1100 $cm^{-1}$ and Mn—H stretches may be assigned at 1470 $cm^{-1}$ and 1580-1630 $cm^{-1}$.

Figure 4:
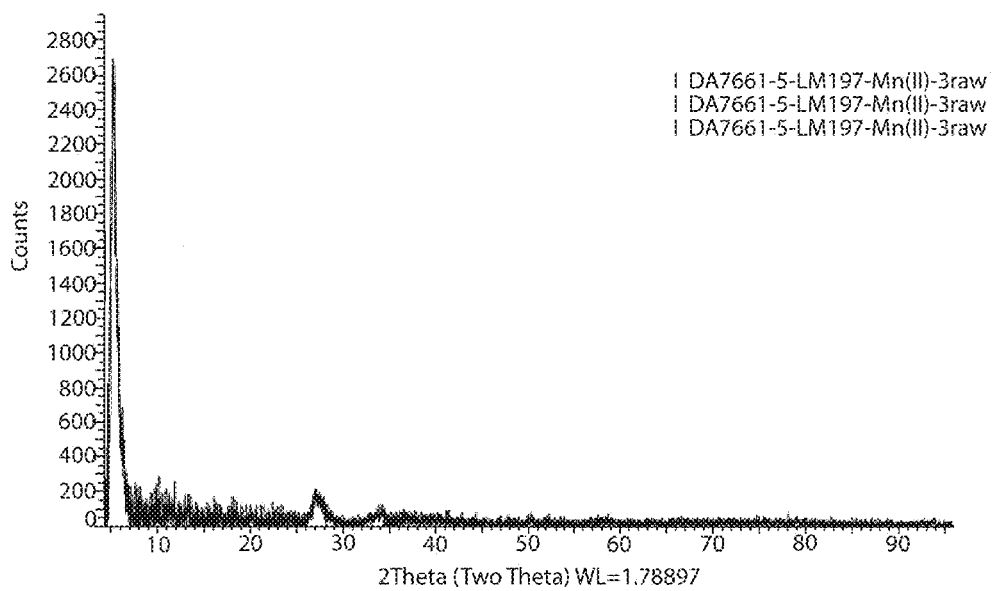
FIG. 4 depicts an X-ray powder diffraction (XRPD) pattern of manganese hydride sample Mnd-150-$H_2$-4 hrs.

The X-ray powder diffraction (XRPD) pattern of manganese hydride sample Mnd-150-$H_2$-4 hrs is shown in FIG. 4. As can be seen from FIG. 4, sample Mnd-150-$H_2$-4 hrs is amorphous. The large peak at approximately 5-6° 2θ is due to an amorphous mesostructure of the glass and/or the amorphous mesostructure of the sample. The minor peaks at approximately 27 and 34° 2θ may be assigned to the glass capilliary.

Figure 5:
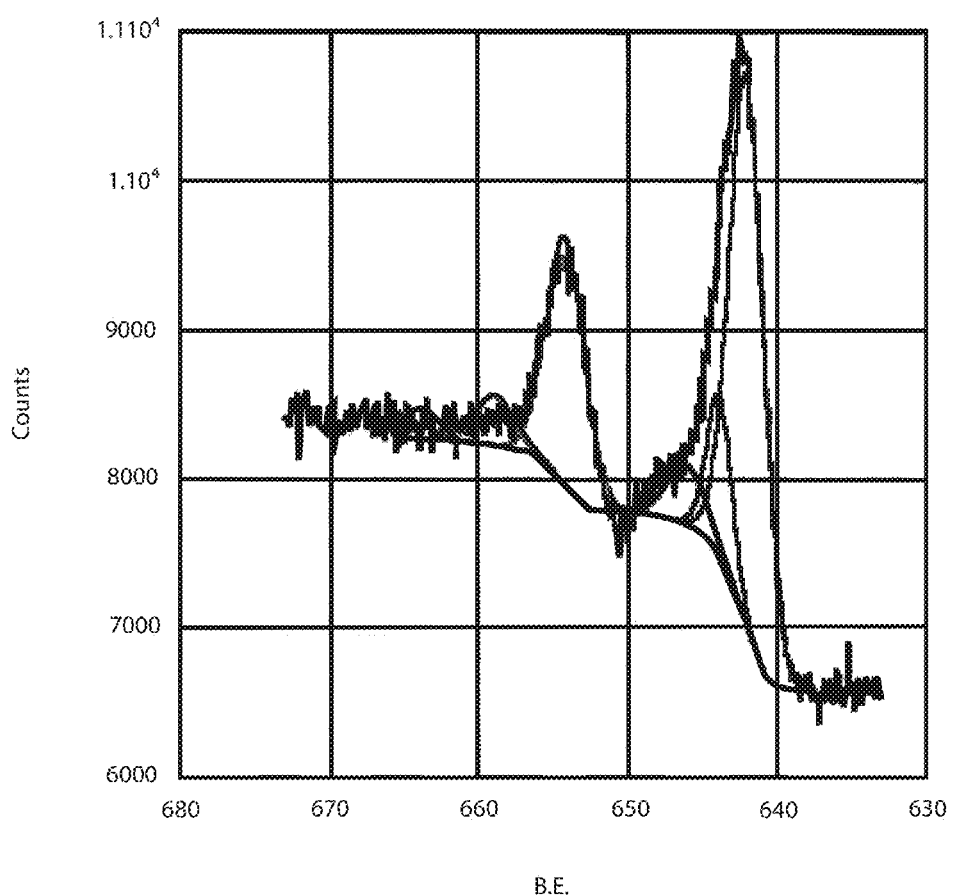
FIG. 5 depicts the valence region of an X-ray photoelectron spectroscopy (XPS) spectrum for manganese hydride sample Mnd-150-$H_2$-4 hrs.

The X-ray photoelectron spectroscopy (XPS) spectrum (2P3/2 region) for manganese hydride sample Mnd-150-$H_2$-4 hrs is shown in FIG. 5. The major emission at 641.9 eV is consistent with Mn (II). The smaller emissions at 643.89 and 646.11 eV may be attributed to higher manganese oxidation states. The XPS is consistent with the sample containing no elemental manganese metal.

Figure 6:
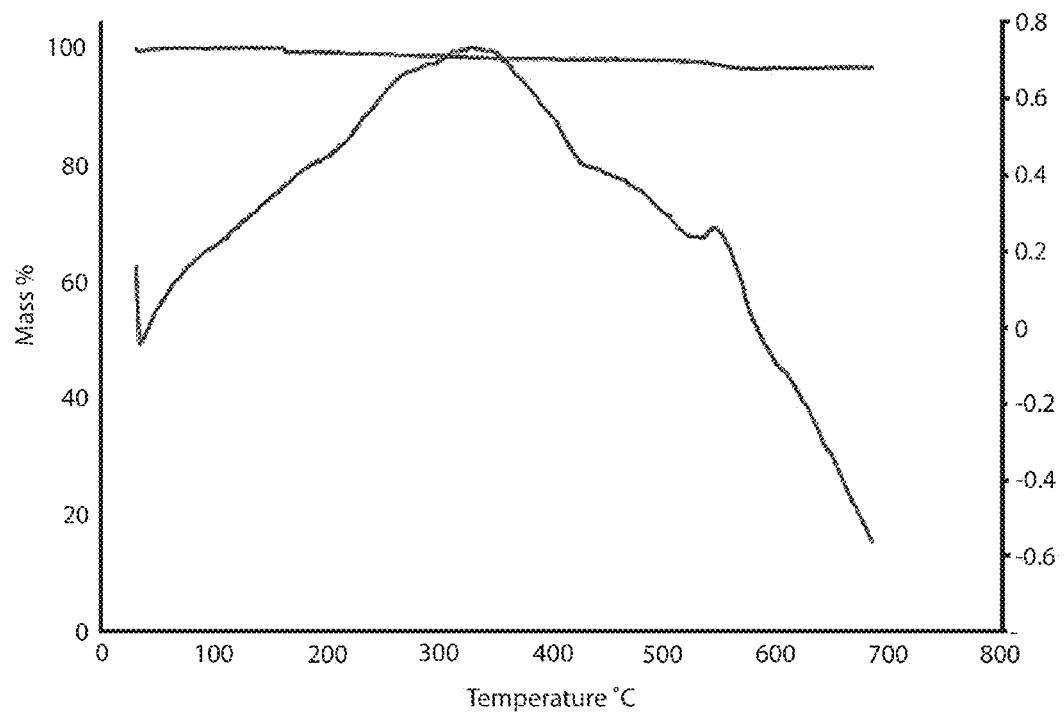
FIG. 6 depicts the differential thermal analysis (DTA) (bottom trace) and thermogravimetric analysis (TGA) (top trace) spectra for manganese hydride sample Mnd-150-$H_2$-4 hrs.

FIG. 6 depicts the differential thermal analysis (DTA) (top trace) and thermogravimetric analysis (TGA) (bottom trace) spectra for manganese hydride sample Mnd-150-$H_2$-4 hrs. The sample retained 97.26% of its mass after heating to 684° C.

Hydrogen Adsorption-Desorption Studies

Figure 7:
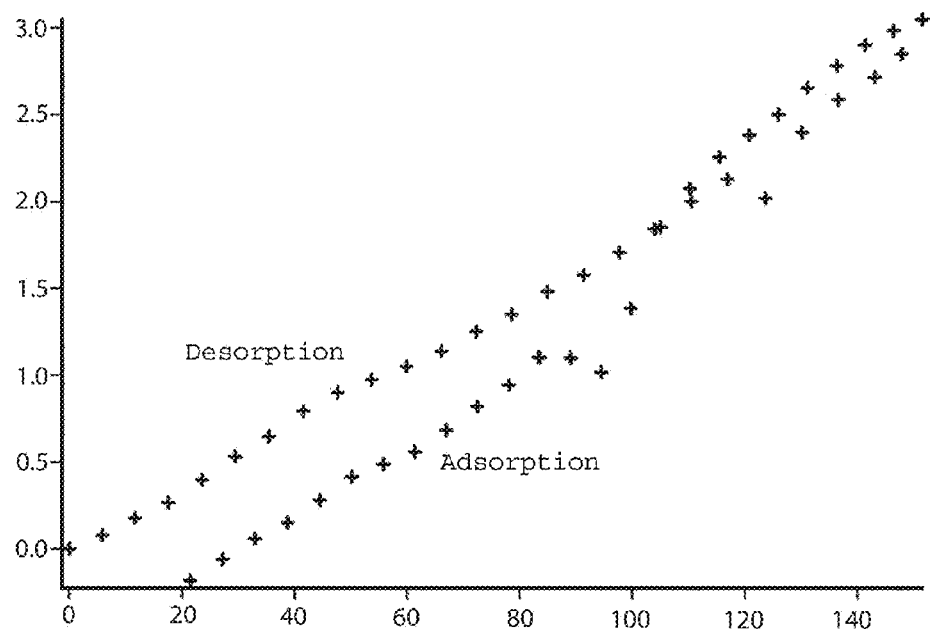
FIG. 7 depicts a hydrogen adsorption-desorption isotherm at 298 K (150 bar) for manganese hydride sample Mnd-100.

A PCT (Pressure-Composition-Temperature) hydrogen adsorption-desorption measurement was performed on sample Mnd-100. Sample Mnd-100 (42.8 mg) reached 3 wt. % hydrogen storage (150 bar) at 298 K. The hydrogen adsorption-desorption isotherm for sample Mnd-100 is shown in FIG. 7. As can be seen from FIG. 7, there is a slight hysteresis between the adsorption and desorption isotherms.

Figure 8:
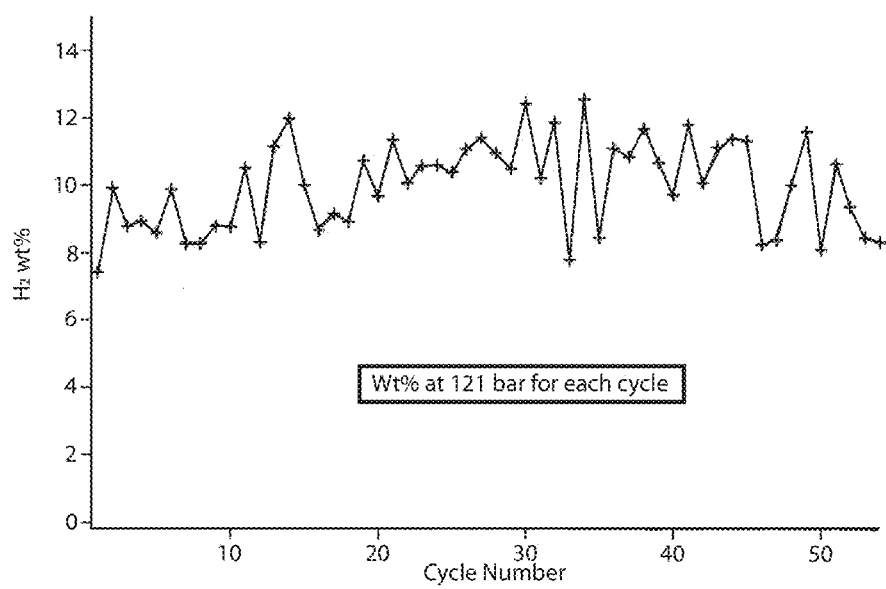
FIG. 8 depicts the life cycle hydrogen adsorption (wt. %) for 53 absorption-desorption cycles at 121 bar $H_2$ for manganese hydride sample Mnd-150-$H_2$-4 hrs.

Subsequently, sample Mnd-100 was hydrogenated in the solid state using the PCT-Pro instrument at 85 bar $H_2$ and 150° C. for four hours. After evacuation for two hours at 100° C. and cooling to room temperature, the resulting sample (Mnd-150-H$_2$-4 hrs) was retested. The sample was not reweighed before measurement. However, after running a PCT life cycle (53 cycles) the sample was reweighed and the resulting isotherms adjusted accordingly. The performance improved with cycling even without scaling the weight, indicating that further loss of hydrocarbon with cycling positively affected performance before loss of weight was compensated for. Thus, the starting value of the raw data before scaling was 3.5 wt % at 150 bar before weight correction, and approximately 5 wt % at 120 bar on cycle 53. Since further weight was lost during cycling, the values at the beginning scaled to the final weight may not be accurate, and the best indication of performance will be the average over the last ten cycles. The sample lost 21.3 mg (50%) of its weight over 53 cycles at 120-150 bar (see FIGS. 8 and 9) due to hydrogenolysis of hydrocarbon ligands from the material. As a result of this further loss of hydrocarbon from the material, the hydrogen storage performance significantly improved, reaching 10 wt. % at 120 bar. The accuracy of this value was established by comparing the results to those of a blank AX-21 sample absorbing the same mmol of H$_2$ at the same pressure.

Figure 9:
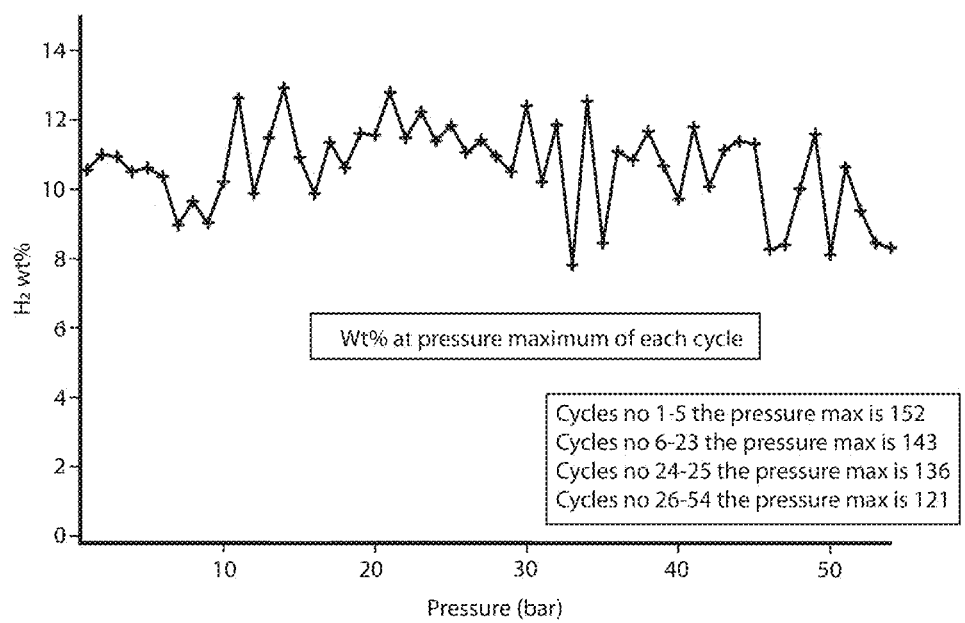
FIG. 9 depicts the life cycle hydrogen adsorption (wt. %) for 53 absorption-desorption cycles at the pressure maximum of each absorption-desorption cycle for manganese hydride sample Mnd-150-$H_2$-4 hrs.

The PCT life cycle measurement was run for 53 adsorption and desorption cycles in total with a ten-minute evacuation of the sample between each cycle. At the start of the experiment, the pressure maximum of each cycle was set to 150 bar but due to consumption of the test gas the pressure maximum for each cycle had to be reduced. The wt. % of H$_2$ adsorbed by the sample at 121 bar in each cycle is shown below in FIG. 8. The wt. % at the pressure maximum of each cycle is shown in FIG. 9.

The fluctuations in cycling may be due to error associated with the random noise in the pressure transducer visible due to the small sample size.

The H$_2$ storage performance of the material did not decay over the course of the 53 cycles, which is an important property for commercialisation of hydrogen storage materials for vehicle applications.

Figure 10:
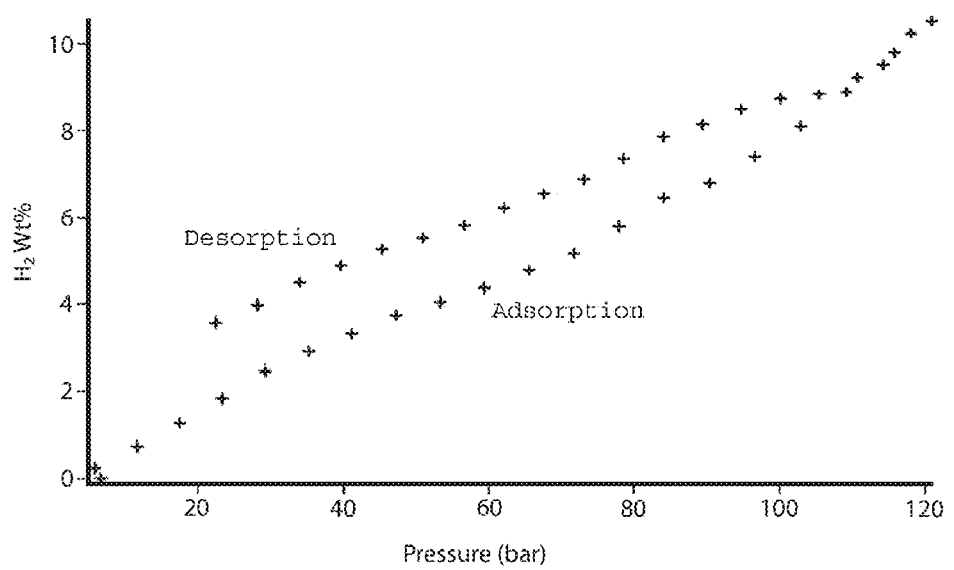
FIG. 10 depicts a hydrogen adsorption-desorption isotherm at 298 K for manganese hydride sample Mnd-150-$H_2$-4 hrs.

FIG. 10 shows the PCT hydrogen adsorption-desorption isotherm recorded after the 53 life cycle measurements, showing that there is some hysteresis between adsorption and desorption.

Figure 11:
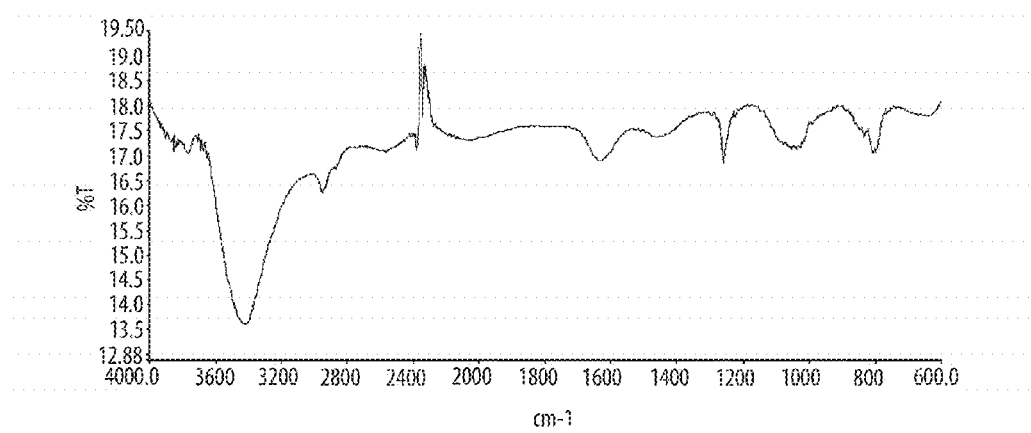
FIG. 11 depicts the IR spectrum of manganese hydride sample Mnd-150-$H_2$-4 hrs following 53 absorption-desorption cycles at 120-150 bar $H_2$.

After solid state hydrogenation of sample Mnd-100 at 150° C. and 85 bar H$_2$ for four hours to afford sample Mnd-150-H$_2$-4 hrs and subsequent exposure to 53 cycles of adsorption and desorption at 120-150 bar, the IR spectrum was recorded to determine the extent of loss of hydrocarbon. As can be seen from FIG. 11, the stretches at 1630 cm$^{-1}$ and 1460 cm$^{-1}$ assigned to Mn—H have increased in intensity as neopentyl ligands have been replaced by hydride ligands. There has also been a reduction in the intensity and number of C—H stretches. The low intensity C—H stretch at approx. 2800 cm$^{-1}$ arises from residual hydrocarbon remaining in the framework of the material. The presence of this low intensity C—H and the fact that saturation was not reached at 120 bar implies that higher capacity may be possible. This is further supported by the observation that saturation was not reached in the isotherm shown in FIG. 10.

Figure 12:
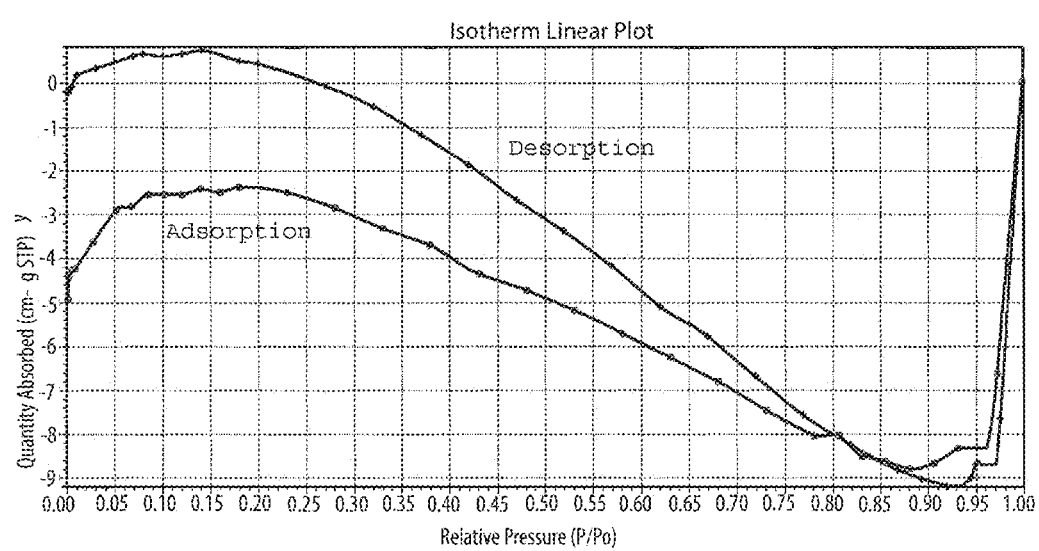
FIG. 12 depicts a nitrogen adsorption-desorption isotherm for manganese hydride sample Mnd-150-$H_2$-4 hrs following 53 absorption-desorption cycles at 120-150 bar $H_2$.

The nitrogen adsorption-desorption isotherm (77K) for sample Mnd-150-H$_2$-4 hrs following 53 cycles of adsorption and desorption at 120-150 bar H$_2$ is shown in FIG. 12. The material after cycling exhibits a low BET surface area of 1.4 m$^2$/g. The N$_2$ adsorption-desorption isotherm does decrease into negative values, due to the small amount of sample used for this measurement. This indicates that hydrogen is able to diffuse through the structure without pores visible on the nitrogen adsorption size regime. Such diffusion of hydrogen is common in amorphous materials, and often occurs without significant volume change (hydrogen diffusion through amorphous Pd films, for example). This would be advantageous for any hydrogen storage system because it means that volume changes would not have to be taken into account.

Figure 13:
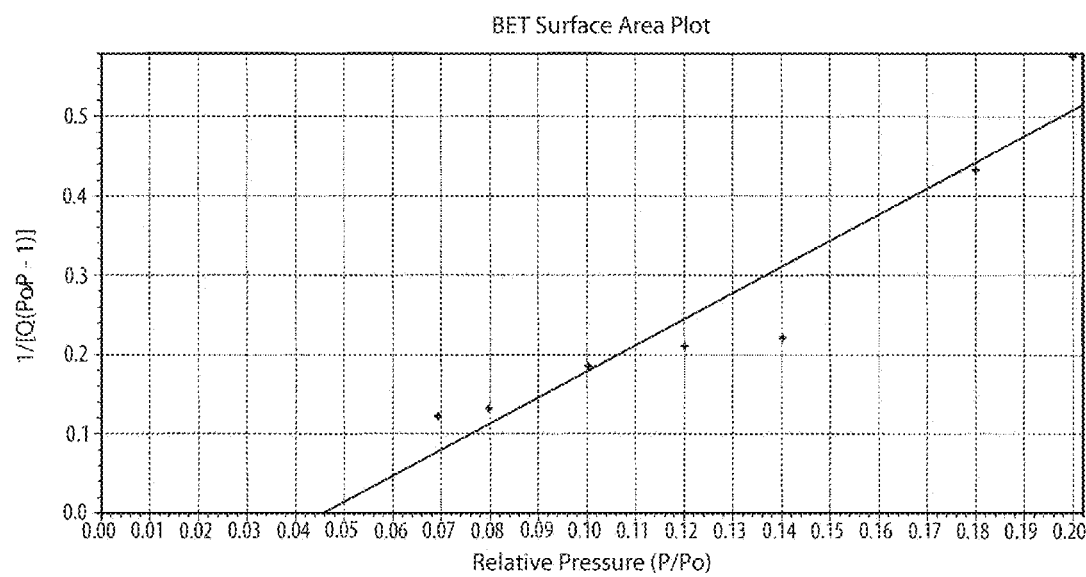
FIG. 13 depicts a BET plot for manganese hydride sample Mnd-150-$H_2$-4 hrs following 53 absorption-desorption cycles at 120-150 bar $H_2$.

FIG. 13 shows the BET plot of sample Mnd-150-H$_2$-4 hrs after 55 cycles of adsorption and desorption at 120-150 bar H$_2$.

Theoretically, a hydrogen adsorption of 10.5 wt % would correspond to formation of MnH$_8$, 7.0 wt % would correspond to formation of MnH$_6$ and 3.5 wt % would correspond to formation of MnH$_4$. However, as discussed above, the metal hydrides described herein are not strictly stoichiometric. A hydrogen adsorption of 14 wt % would correspond to formation of MnH$_{10}$. While the existence and structure of MnH$_{10}$ may seem surprising from a solid state chemistry perspective, rhenium, the congener of Mn, forms Re(VII)H$_7$ and Na$_2$Re(VII)H$_9$ (see, e.g., Parker et al., *Inorg. Chem.*, 45, 10951-10957, 2006; Abrahams et al., *Inorg. Chem.*, 3, 558-567, 1964) and it is typical for the first row transition metal to prefer a lower oxidation state. As these rhenium compounds are stable Re(VII) species, metastable manganese analogues in which the hydrides could exist predominantly as Kubas ligands to preserve the preferred lower oxidation state of manganese, may be envisaged.

Furthermore, on the basis of (R$_3$P)$_2$Ru(II)H$_6$ (see, e.g., Grellier et al., *Angewandte Chemie Int. Ed.*, 46, 2613-2615, 2007), a compound with two axial phosphines, two hydrides, and two Kubas H$_2$ ligands, the structure of MnH$_{10}$ can be rationalized by replacing each phosphine with a Kubas H$_2$. Without being bound by theory, this suggests that the solid amorphous polymeric MnH$_2$ described herein may be effectively "solvated" by Kubas H$_2$ units at high pressure to reversibly form Mn(H$_2$)$_n$ (n=2, 3, 4, 5). The expected density of MnH$_2$ would be close to CaH$_2$ (~2 g/cc) which translates into 280 Kg/m$^3$ volumetric density for MnH$_{10}$, four times the ultimate U.S. Department of Energy target in this category.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A bulk solid comprising a metal hydride of the formula (I):

$$Mn(M^2)_zH_xR_yL_n \qquad (I)$$

wherein
M$^2$ is one or more metals (other than manganese), which have a total content of z;
R, if present, is an organic group;
L is a Lewis base;
n is 0 to about 1;
x is about 1.5 to about 10;
y is 0 to about 0.25; and
z is 0 to about 1;
wherein the metal hydride is stable as a bulk solid at room temperature, and wherein the metal hydride is capable of storing molecular hydrogen in an amount of at least 2% (based upon 100% total weight of the metal hydride without hydrogen stored in it) and reversibly releasing the hydrogen.

2. The bulk solid according to claim 1, wherein x is selected from the group consisting of (i) about 1.8 to about 2.2, (ii) about 2.2 to about 2.8, (iii) about 2.8 to about 3.2, (iv) about 3.2 to about 3.8, (v) about 3.8 to about 4.2, (vi) about 4.2 to about 4.8, (vii) about 4.8 to about 5.2, (viii) about 5.2 to about 6.8), (ix) about 6.8 to about 7.2, (x) about 7.2 to about 7.8, (xi) about 7.8 to about 8.2, (xii) about 8.2 to about 8.8, (xiii) about 8.8 to about 9.2, (xiv) about 9.2 to about 9.8, and (xv) about 9.8 to about 10.2.

3. The bulk solid according to claim 1, wherein x is selected from the group consisting of (i) about 1.8 to about 2.2, (ii) about 3.8 to about 4.2, (iii) about 5.8 to about 6.2, (iv) about 7.8 to about 8.2 and (v) about 9.8 to about 10.2.

4. The bulk solid according to claim 1, wherein x is about 1.8 to about 2.2.

5. The bulk solid according to claim 1, wherein x is about 2.8 to about 3.2.

6. The bulk solid according to claim 1, wherein x is about 3.8 to about 4.2.

7. The bulk solid according to claim 1, wherein x is about 4.8 to about 5.2.

8. The bulk solid according to claim 1, wherein x is about 5.8 to about 6.2.

9. The bulk solid according to claim 1, wherein x is about 6.8 to about 7.2.

10. The bulk solid according to claim 1, wherein x is about 7.8 to about 8.2.

11. The bulk solid according to claim 1, wherein x is about 8.8 to about 9.2.

12. The bulk solid according to claim 1, wherein x is about 9.8 to about 10.2.

13. The bulk solid according to claim 1, wherein when x is greater than about 2, the material is at a pressure of about 10 bar or more of hydrogen.

14. The bulk solid according to claim 1, wherein y is not 0 and R does not contain a β hydrogen substituent.

15. The bulk solid according to claim 14, wherein R is mesityl, neopentyl, trimethylsilylmethyl or benzyl.

16. The bulk solid according to claim 1, wherein y is selected from the group consisting of (i) less than about 0.2, (ii) less than about 0.1, (iii) less than about 0.05, (iv) less than about 0.01, and (v) less than about 0.005.

17. The bulk solid according to claim 1, wherein y is 0.

18. The bulk solid according to claim 1, wherein n is not 0 and L is selected from the group consisting of an organic solvent, water, H$_2$S, an amine, a phosphine, a sulfide, and combinations thereof.

19. The bulk solid according to claim 18, wherein L is selected from the group consisting of diethylether, THF, dioxane, and combinations thereof.

20. The bulk solid according to claim 1, wherein n is selected from the group consisting of (i) 0 to about 0.8, (ii) 0 to about 0.6, (iii) 0 to about 0.5, (iv) 0 to about 0.4, (v) 0 to about 0.2, (vi) 0 to about 0.1, (vii) 0 to about 0.05 and (viii) 0 to about 0.01.

21. The bulk solid according to claim 1, wherein n is 0.

22. The bulk solid according to claim 1, wherein the metal hydride is free or substantially free of metal ions other than manganese and/or free or substantially free of organic residue.

23. The bulk solid according to claim 1, wherein the bulk solid is used for hydrogen storage.

24. The bulk solid according to claim 1, wherein the metal hydride is substantially amorphous.

25. The bulk solid according to claim 1, wherein the metal hydride is crystalline.

26. A metal hydride storage material comprising a bulk solid according to claim 1.

27. A bulk solid according to claim 1, prepared by a process comprising
(a) preparing a manganese alkyl compound of formula (III):

$$MnR_xY_yL_n \qquad (III)$$

wherein
R is an organic group;
L is a Lewis base;
n is 0 to about 1;
Y, if present, is an alkali metal, an alkaline earth metal, or any combination thereof;
x is about 1.8 to about 2.2; and
y is 0 to about 0.2;
by a process comprising reacting a compound of the formula MnX$_2$(dioxane)$_z$ with an alkyl alkali metal compound, an alkyl alkaline earth metal compound, or any combination thereof;
wherein z is about 1 to about 2; and
X is halide; and
(b) converting the manganese alkyl compound of formula (III) to the bulk solid.

28. A process for purifying a bulk solid according to claim 1, said process comprising comprises subjecting the metal hydride to one or more hydrogen adsorption-desorption cycles.

29. The process according to claim 28, wherein said metal hydride is subjected to about 10 or more hydrogen adsorption-desorption cycles.

30. The process according to claim 28, wherein said metal hydride is subjected to about 50 or more hydrogen adsorption-desorption cycles.

31. The process according to claim 28, wherein the hydrogen adsorption-desorption cycles are conducted at a hydrogen pressure of between about 50 bar and about 170 bar.

32. A method of storing hydrogen comprising:
providing a bulk solid according to claim 1;
adding hydrogen to the bulk solid; and
allowing the hydrogen to coordinate to the bulk solid.

33. The method according to claim 32, wherein the hydrogen is stored in a storage system.

34. The method according to claim 32, wherein when x is greater than about 2, the bulk solid is at a pressure of about 10 bar or more of hydrogen.

35. The method according to claim 32, further comprising releasing the hydrogen from the bulk solid.

36. The method according to claim 35, wherein the hydrogen is released from the bulk solid by reducing the pressure of the hydrogen, increasing the temperature, or a combination thereof.

37. A storage system for a gas selected from hydrogen, methane and compressed natural gas comprising a storage system and a bulk solid according to claim 1 within the storage system.

38. A storage system for producing electricity using a fuel-cell or heat using an oxidant, comprising a storage system and a bulk solid according to claim 1 within the storage system.

39. The storage system of claim 38, wherein the system is portable.

40. A battery comprising a bulk solid according to claim 1.

41. A pellet comprising a bulk solid according to claim 1 and a porous carbon.

42. The bulk solid according to claim 1, wherein the metal hydride contains a transition metal in more than one oxidation state.

43. The bulk solid according to claim 1, wherein the metal hydride is substantially amorphous.

44. The bulk solid according to claim 1, wherein z is not 0 and $M^2$ is selected from lithium, sodium, potassium, aluminum, boron, magnesium, calcium, beryllium, iron, vanadium, chromium, cobalt, copper, zinc, gallium, nickel, zirconium, niobium, molybdenum, technetium, ruthenium, rhodium, palladium, silver, cadmium, hafnium, tantalum, tungsten, rhenium, osmium, iridium, platinum, gold, mercury, and combinations thereof.

45. A bulk solid comprising a metal hydride of the formula (I):

$$Mn(M^2)_z H_x R_y L_n \qquad (I)$$

wherein
- $M^2$ is one or more metals (other than manganese), which have a total content of z;
- R, if present, is an organic group;
- L is a Lewis base;
- n is 0 to about 1;
- x is about 1.5 to about 10;
- y is 0 to about 0.25; and
- z is 0 to about 1;

wherein the metal hydride is stable as a bulk solid at room temperature,
the metal hydride is substantially amorphous; and
the metal hydride is capable of storing and reversibly releasing molecular hydrogen ($H_2$).

46. A bulk solid comprising a metal hydride of the formula (I):

$$Mn(M^2)_z H_x R_y L_n \qquad (I)$$

wherein
- $M^2$ is one or more metals (other than manganese), which have a total content of z;
- R, if present, is an organic group;
- L is a Lewis base;
- n is 0 to about 1;
- x is about 1.5 to about 10;
- y is 0 to about 0.25; and
- z is 0 to about 1;

wherein the metal hydride is stable as a bulk solid at room temperature;
the metal hydride is capable of storing and reversibly releasing molecular hydrogen ($H_2$); and
$M^2$ is selected from lithium, sodium, potassium, aluminum, boron, magnesium, calcium, beryllium, iron, vanadium, chromium, cobalt, copper, zinc, gallium, nickel, zirconium, niobium, molybdenum, technetium, ruthenium, rhodium, palladium, silver, cadmium, hafnium, tantalum, tungsten, rhenium, osmium, iridium, platinum, gold, mercury, and combinations thereof.

47. The bulk solid according to claim 46, wherein the metal hydride is substantially amorphous.

* * * * *